(12) United States Patent
Okada et al.

(10) Patent No.: US 10,335,306 B2
(45) Date of Patent: Jul. 2, 2019

(54) SUPPORTER

(71) Applicants: Kowa Company, Ltd., Aichi (JP); Advancing Inc., Osaka (JP); DMChain Cooperative, Ishikawa (JP)

(72) Inventors: Hidetaka Okada, Tokyo (JP); Hitoshi Ojima, Osaka (JP); Hidenori Kaseno, Ishikawa (JP)

(73) Assignees: KOWA CO., LTD (JP); ADVANCING INC. (JP); DMCHAIN COOPERATIVE (JP)

( * ) Notice: Subject to any disclaimer, the term of this patent is extended or adjusted under 35 U.S.C. 154(b) by 1215 days.

(21) Appl. No.: 14/298,346

(22) Filed: Jun. 6, 2014

(65) Prior Publication Data
US 2014/0288474 A1 Sep. 25, 2014

Related U.S. Application Data

(63) Continuation of application No. PCT/JP2012/081775, filed on Dec. 7, 2012.

(30) Foreign Application Priority Data

Dec. 9, 2011 (JP) ................. 2011-270553
Apr. 6, 2012 (JP) ................. 2012-087298

(51) Int. Cl.
*A61F 5/02* (2006.01)
*A61F 5/03* (2006.01)
*A61F 5/00* (2006.01)

(52) U.S. Cl.
CPC .............. *A61F 5/028* (2013.01); *A61F 5/024* (2013.01); *A61F 5/03* (2013.01)

(58) Field of Classification Search
CPC .......... A61F 13/49011; A61F 13/49012; A61F 13/5638; A61F 13/496; A61F 13/15593;
(Continued)

(56) References Cited

U.S. PATENT DOCUMENTS 2,117,309 A * 5/1938 Fritsch ...................... A61F 5/03
450/119
3,096,760 A 7/1963 Nelkin
(Continued)

FOREIGN PATENT DOCUMENTS

GB 956754 4/1964
JP 06-037316 U 5/1994
(Continued)

OTHER PUBLICATIONS

International Search Report for corresponding application No. PCT/JP2012/081775, dated May 10, 2013.
European International Search report dated Jul. 15, 2015 from corresponding International Application No. PCT/US2012/081775.

*Primary Examiner* — Kari K Rodriquez
(74) *Attorney, Agent, or Firm* — Duquette Law Group, LLC

(57) ABSTRACT

A supporter includes a body section having a back-contact section, a first auxiliary band section of which one end is fixed to the top end of a left side of the back-contact section and the other end is fixed to the bottom end of a right side of the back-contact section, a second auxiliary band section forming a pair with the first auxiliary band section, a first ring arranged to slide between the one end and the other end of the first auxiliary band section, a second ring forming a pair with the first ring, a first adjustment band section of which one end is fixed to loops on a right end side of the body section and the other end can be fastened to loops on the right end side of the body section, and a second adjustment band section forming a pair with the first adjustment band section.

20 Claims, 25 Drawing Sheets

(58) Field of Classification Search
CPC ............ A61F 13/49017; A61F 13/4902; A61F 13/15699; A61F 13/49015; A61F 13/474; A61F 13/4942; A61F 13/5616; A61F 13/15707; A61F 13/49001; A61F 13/49466; A61F 13/532; A61F 13/533; A61F 13/5622; A61F 13/68; A61F 13/49; A61F 13/625; A61F 5/028; A61F 13/49006; A61F 13/505; A61F 13/15747; A61F 13/15756; A61F 13/49003; A61F 5/02; A61F 5/022; A61F 5/024; A61F 5/026; A61F 5/03; A44B 18/0003; A44B 18/0049; A61B 2560/0271; A61B 2562/0219; A61B 5/002; A61B 5/0022; A61B 5/0205; A61B 5/0432; A61B 5/0535; A61B 5/1073; A61B 5/1116; A61B 5/1135; A61B 5/6804; B27D 3/04; B29C 55/165; B30B 5/06; B65H 23/022; Y10S 264/73; Y10T 156/1741; A41D 1/08; A45F 3/10; A63B 2071/1241; A63B 2209/10; A63B 2225/09; A63B 2243/0066; A63B 2244/183; A63B 2244/22; A63B 71/1225; A41C 3/00
USPC ......................... 602/19; 2/312–316; 128/96.1
See application file for complete search history.

(56) References Cited

U.S. PATENT DOCUMENTS

| | | | | |
|---|---|---|---|---|
| 3,603,316 | A | * | 9/1971 | Lehman .................... A41C 1/08 2/312 |
| 3,920,008 | A | * | 11/1975 | Lehman .................... A61F 5/03 128/96.1 |
| 3,926,183 | A | * | 12/1975 | Spiro ...................... A61F 5/028 450/94 |
| 3,927,665 | A | | 12/1975 | Wax |
| 4,836,194 | A | * | 6/1989 | Sebastian ................ A61F 5/028 128/DIG. 20 |
| 5,334,134 | A | | 8/1994 | Saunders |
| 5,722,940 | A | | 3/1998 | Gaylord, Jr. et al. |
| 2010/0228170 | A1 | * | 9/2010 | Imai ........................ A61F 5/028 602/19 |

FOREIGN PATENT DOCUMENTS

| | | |
|---|---|---|
| JP | 8182794 | 7/1996 |
| JP | 10277075 A | 10/1998 |
| JP | 2010277075 A | 10/1998 |
| JP | 11104159 A | 4/1999 |
| JP | 2011104159 A | 4/1999 |
| JP | 3067532 U | 4/2000 |
| JP | 2010207436 A | 9/2010 |
| WO | 2010145767 A1 | 12/2010 |

* cited by examiner

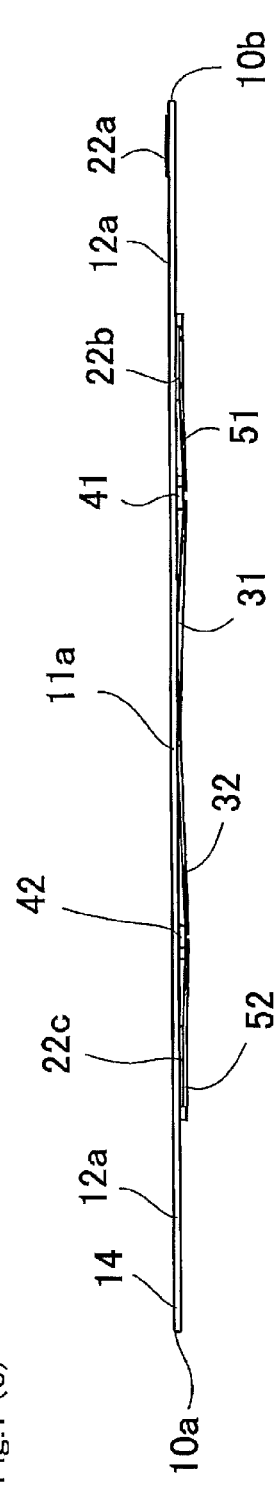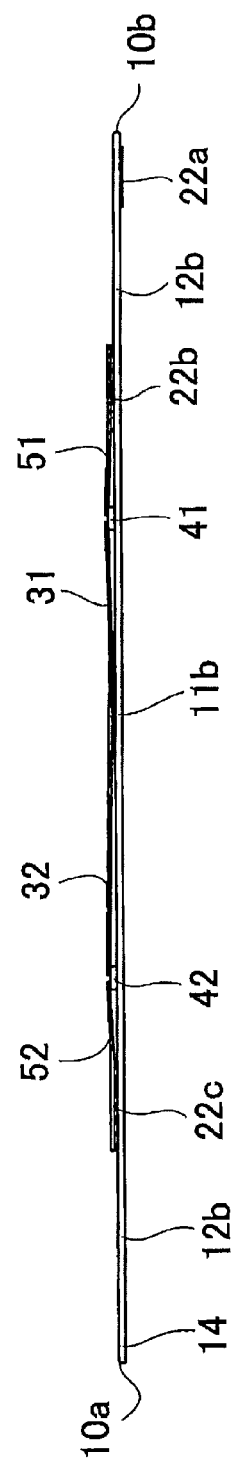

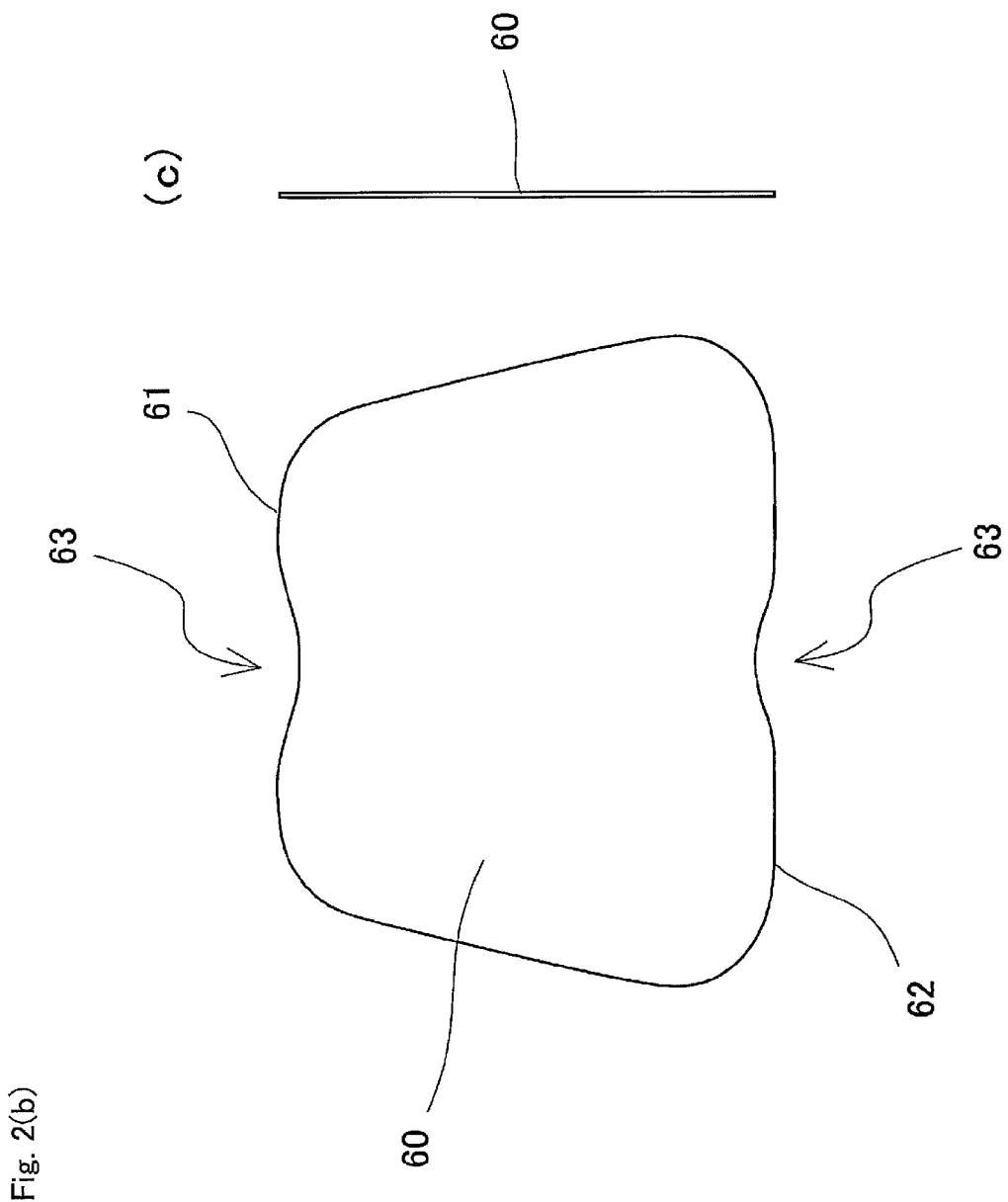

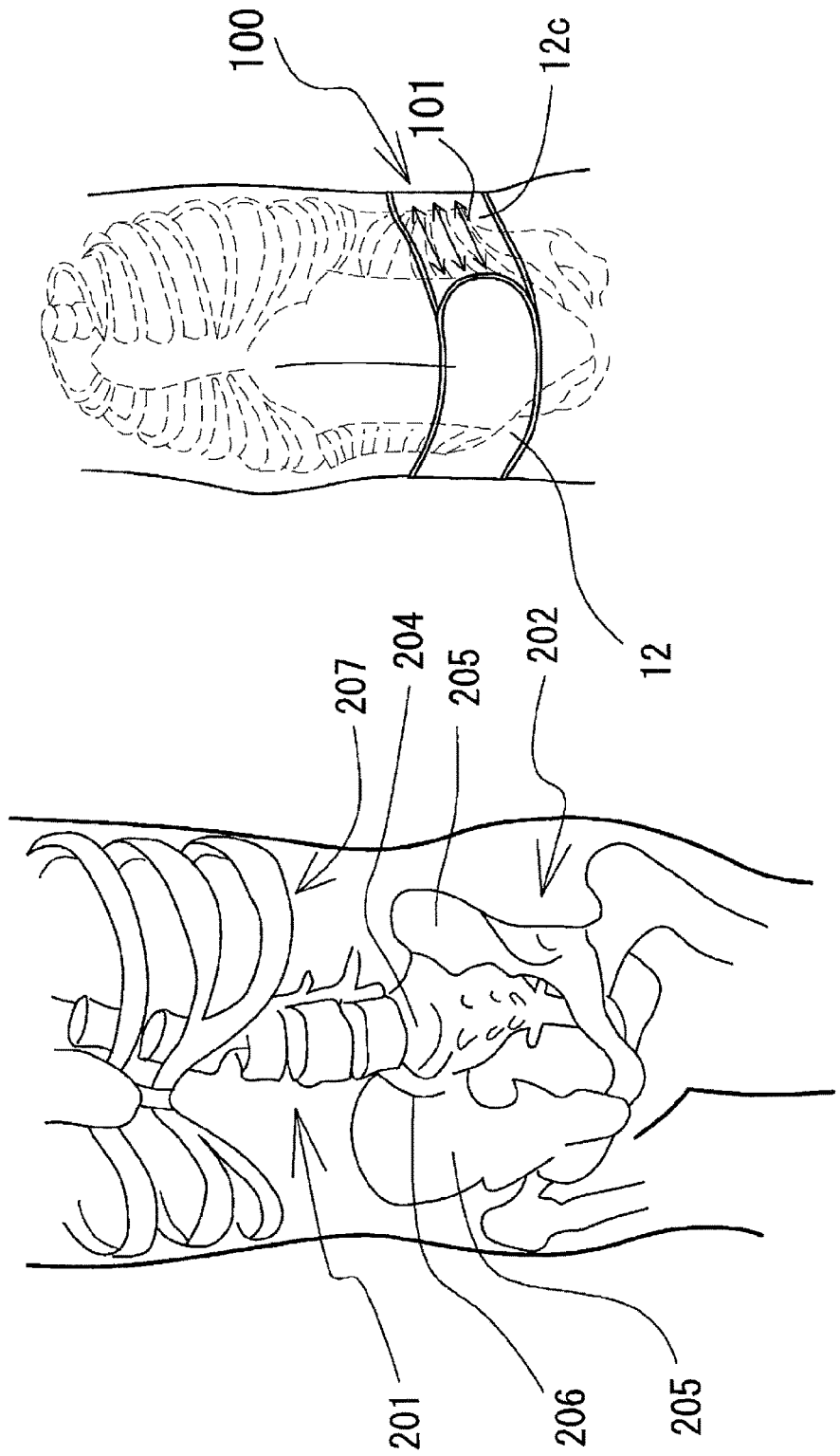

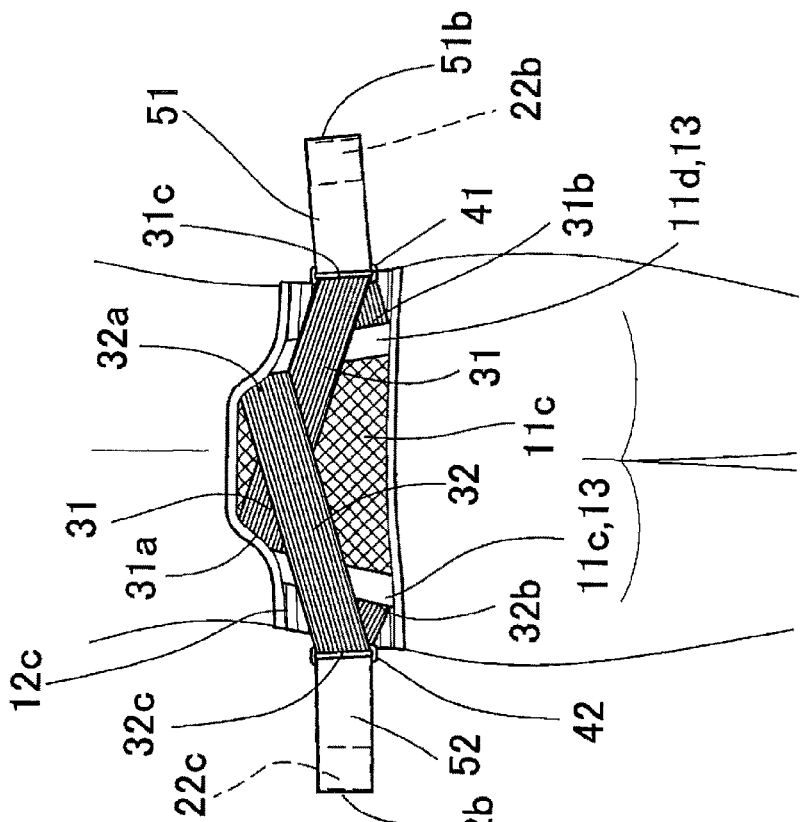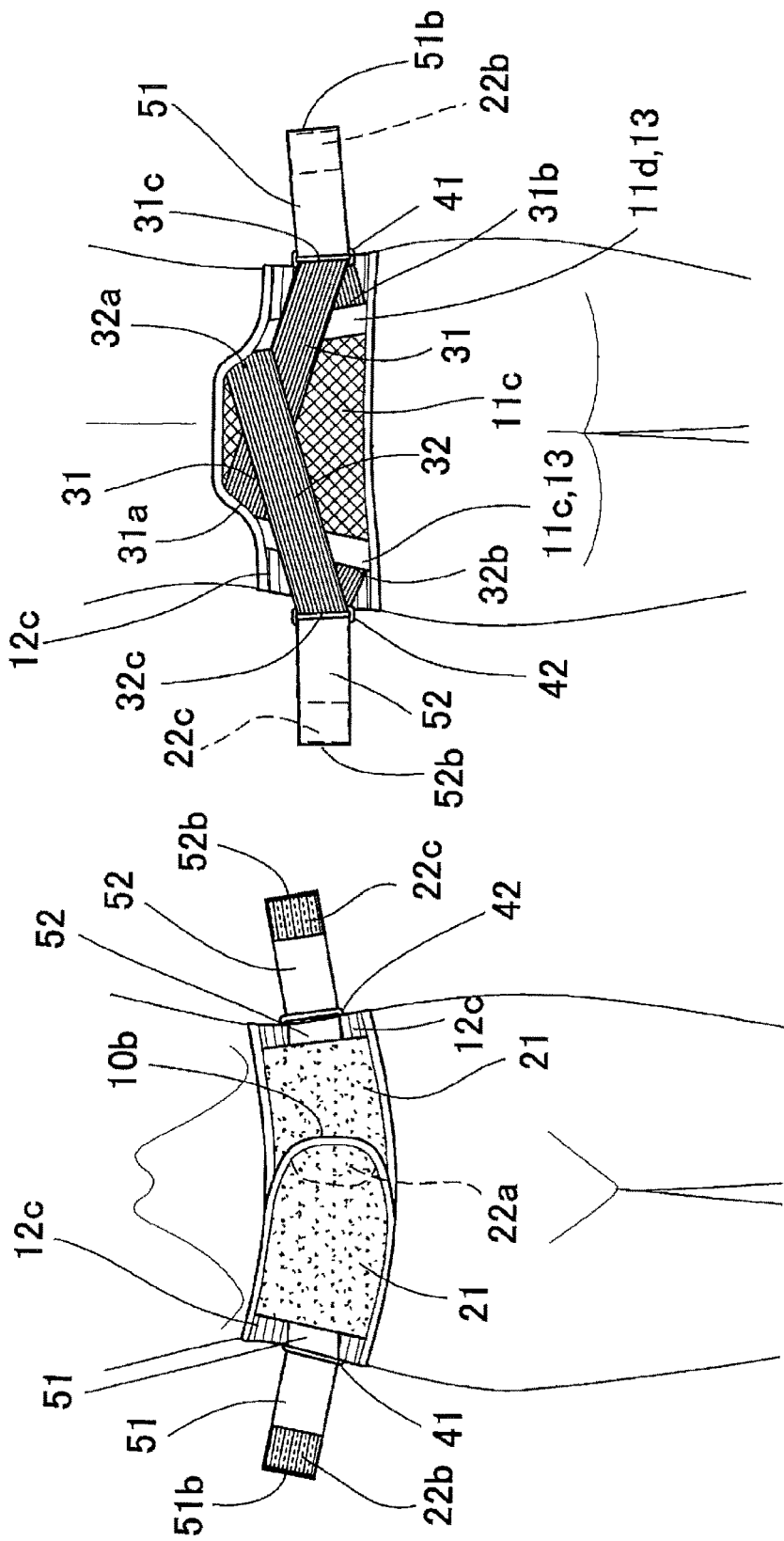
Fig.5 (a)
Fig.5 (b)

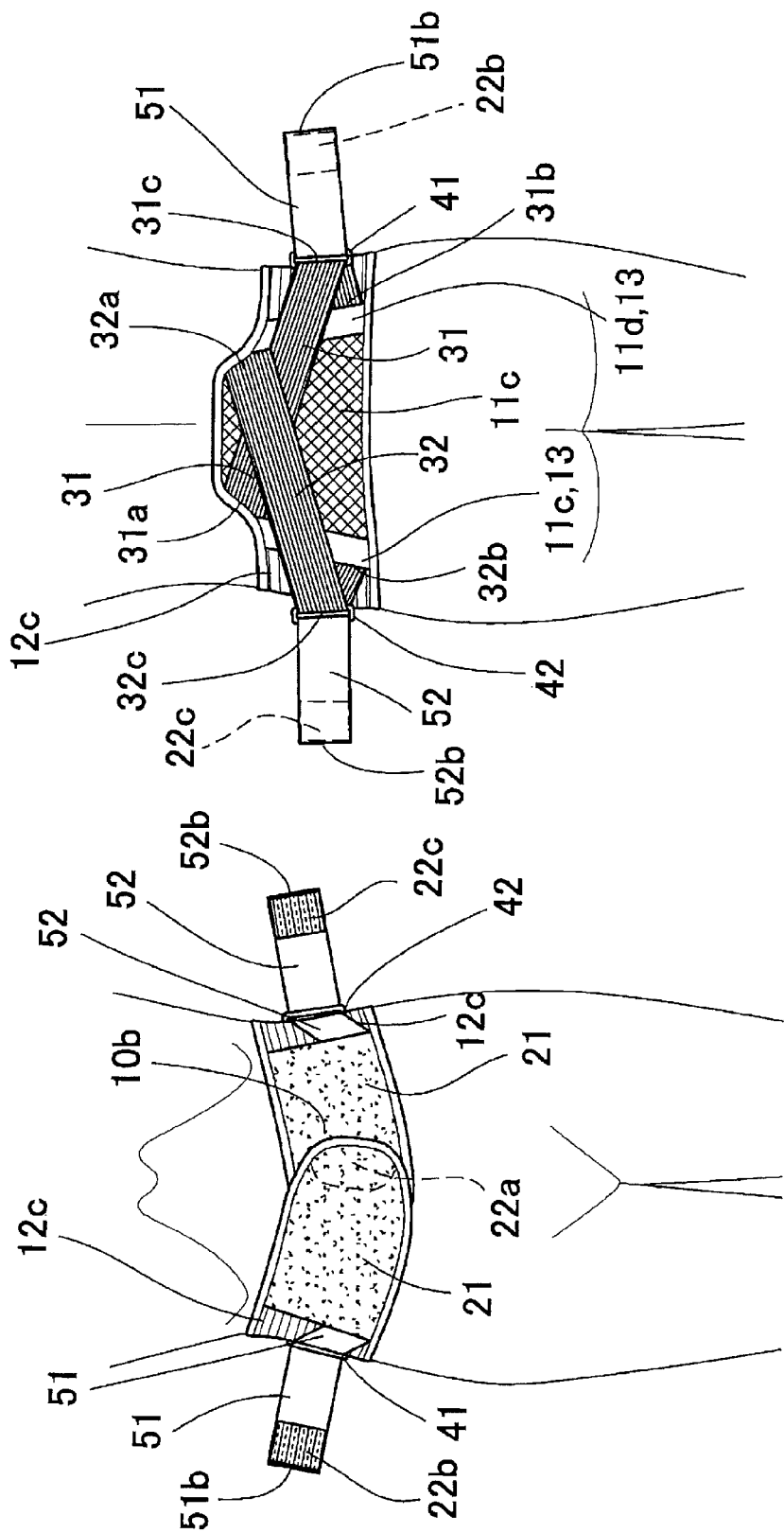

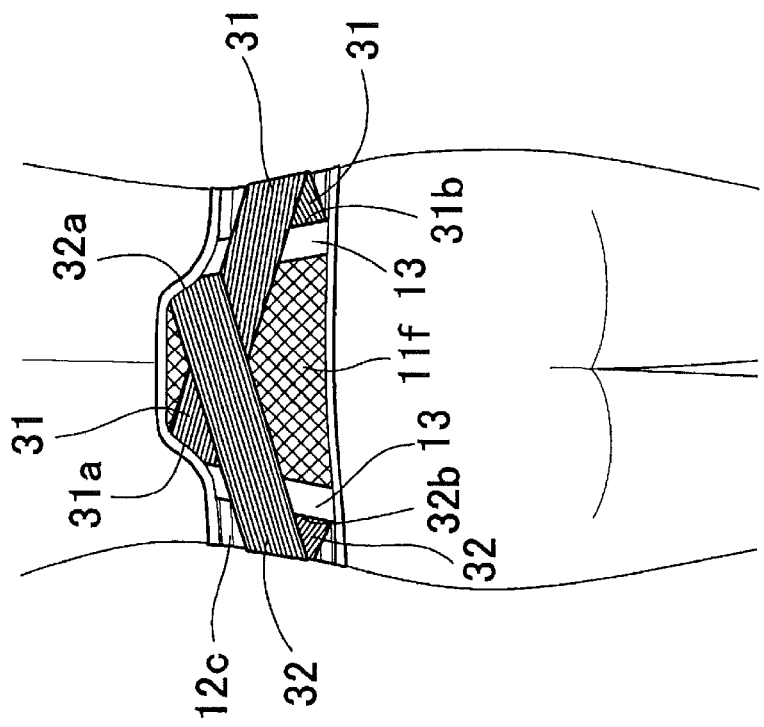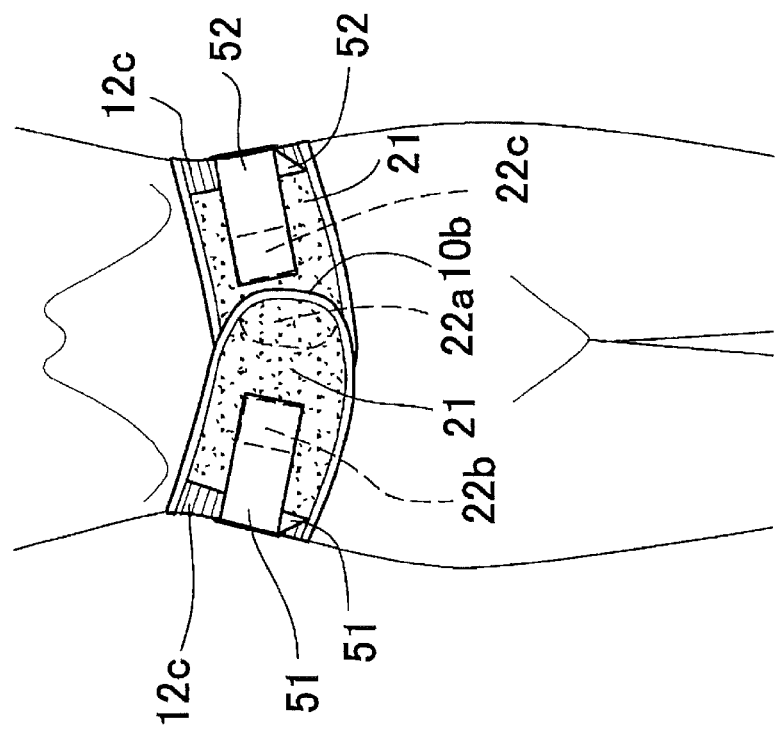
Fig.10 (a)
Fig.10 (b)

SUPPORTER

RELATED APPLICATIONS

This application is a continuation of International Application No. PCT/JP2012/081775, filed Dec. 7, 2012, now pending, which claims priority to Japanese Application No. 2011-270553, filed Dec. 9, 2011 and which claims priority to Japanese Application No. 2012-087298, filed Apr. 6, 2012, the contents of which are incorporated herein by reference.

TECHNICAL FIELD

The present invention relates to a supporter capable of supporting a wearer's daily motions, and more particularly, to a supporter with which an intraperitoneal pressure increasing effect of increasing a pressure of an abdominal cavity to support the lumbar vertebra can be given to a wearer, which can achieve a retroflexion prevention effect of preventing retroflexion of a lumbar region, and which stabilizes a sacroiliac joint.

BACKGROUND

A lumbar band according to the background art includes a band-shaped body section, a fastening belt, and a sling belt, in which the band-shaped body section includes a stretchable portion (a pad fixed thereto) formed of a stretchable material and a non-stretchable portion formed of a substantially non-stretchable material so as to extend from the stretchable portion to both free ends and the ends of a pair of fastening belts are fixed to the central end of the non-stretchable portion (for example, see JP-A-11-104159).

SUMMARY

Technical Problem

In the lumbar band according to the background art, right and left first belts cross each other at two upper and lower positions in the vicinity of the center of a pad, and both ends of each first belt are fixed to the central end of the non-stretchable portion on the same side and are located with the same distance from a ring. Accordingly, when a second belt is drawn to the front side (to a hook-and-loop fastener side), a force is evenly applied to the upper belt and the lower belt of the first belts with respect to the ring and the first belts evenly press the upper and lower parts in the vicinity of the center of the pad.

On the other hand, since a wearer's back region is curved, the lumbar band is separated from the wearer's back region on the upper side of the pad by only causing the first belts to evenly press the upper and lower parts in the vicinity of the center of the pad like the lumbar band according to the background art, thereby not satisfactorily supporting the wearer's lumbar vertebrae.

The present invention is made to solve the above-mentioned problem and an object thereof is to provide a supporter which can prevent separation of the supporter from a wearer's back region at an upper side of a pad to satisfactorily support the wearer's lumbar vertebrae, which can give the wearer an intraperitoneal pressure increasing effect to achieve prevention of retroflexion, and which can stabilize a sacroiliac joint.

Solution to Problem

According to an aspect of the present invention, there is provided a supporter formed of a band-shaped member, the supporter including: a back-contact section that is arranged substantially at the center of the band-shaped member, and that comes in contact with a wearer's back region; protruding sections of which tips protrude upward, and toward right and left from both sides of the back-contact section; a pair of auxiliary band sections that includes two band-shaped members having stretchability in a longitudinal direction and in which an annular ring is arranged to be slidable over each band-shaped member; and a pair of adjustment band sections that includes two band-shaped members having stretchability lower than the stretchability of the auxiliary band sections, wherein each protruding section includes a stretchable portion being in contact with the back-contact section and having stretchability in the longitudinal direction, wherein both ends of the pair of auxiliary band sections are fixed to an upper side of the back-contact section and bottom ends of lateral sides of the back-contact section or bottom ends of the lateral sides in contact with the back-contact section in the stretchable portions of the protruding sections so that the two band-shaped members cross each other, and wherein each of the pair of adjustment band sections is loosely inserted into the annular rings arranged in the auxiliary band sections, one end thereof is fixed to a region other than the stretchable portions of the right and left protruding sections, and the other end thereof includes a fastening portion.

Advantageous Effects of Invention

With the supporter according to the present invention, it is possible to prevent separation of the supporter from a wearer's back region at an upper side of the back-contact section and to satisfactorily support the wearer's lumbar vertebrae.

DETAILED DESCRIPTION

First Embodiment of the Invention

Figure 1:
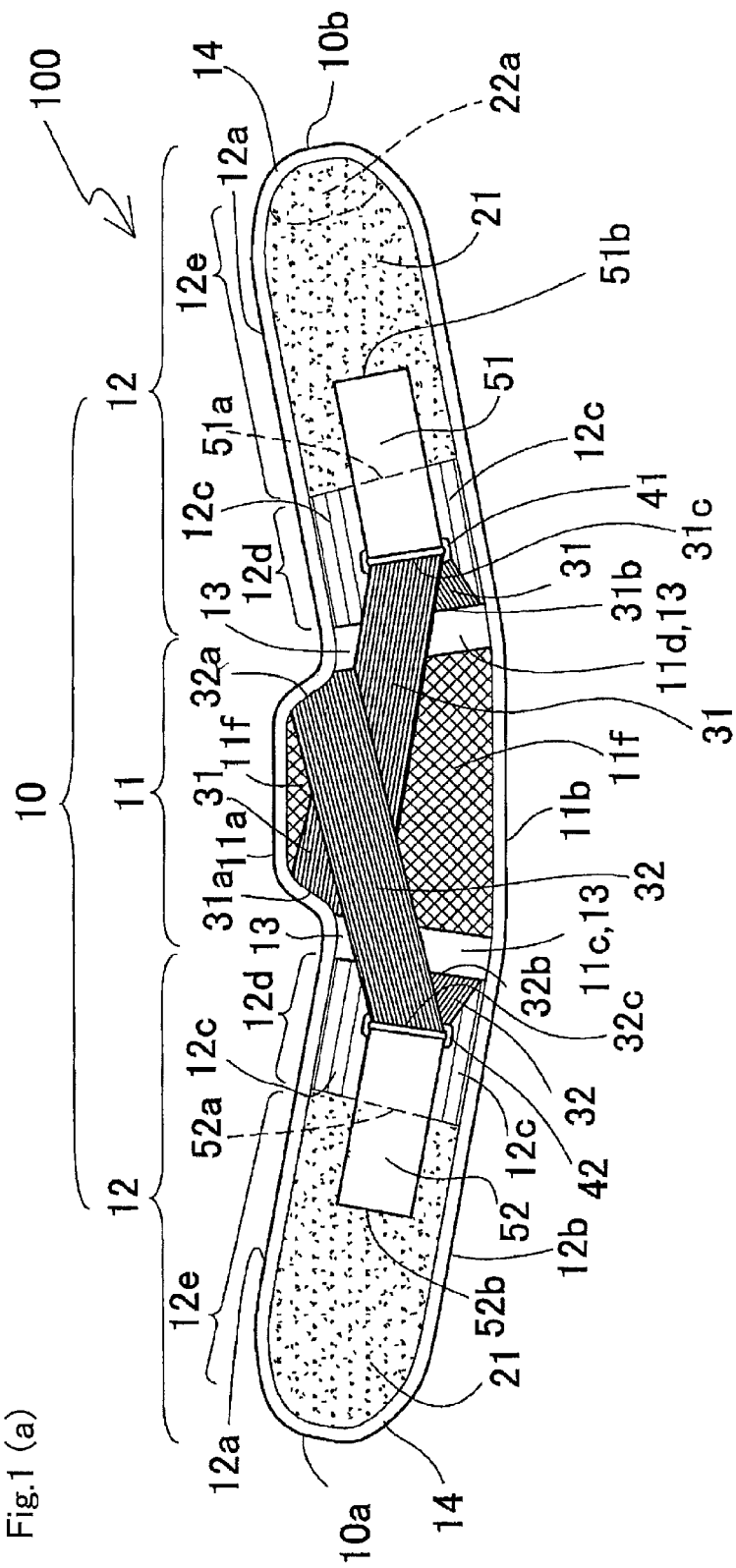
FIG. 1(a) is a diagram illustrating a front surface of a supporter according to a first embodiment.
FIG. 1(b) is a diagram illustrating a lining surface of the supporter illustrated in FIG. 1(a)
FIG. 1(c) is a left side view of the supporter illustrated in FIG. 1(a)
FIG. 1(d) is a right side view of the supporter illustrated in FIG. 1(a)
FIG. 1(e) is an upper side view of the supporter illustrated in FIG. 1(a)
FIG. 1(f) is a lower side view of the supporter illustrated in FIG. 1(a).
Figure 1:
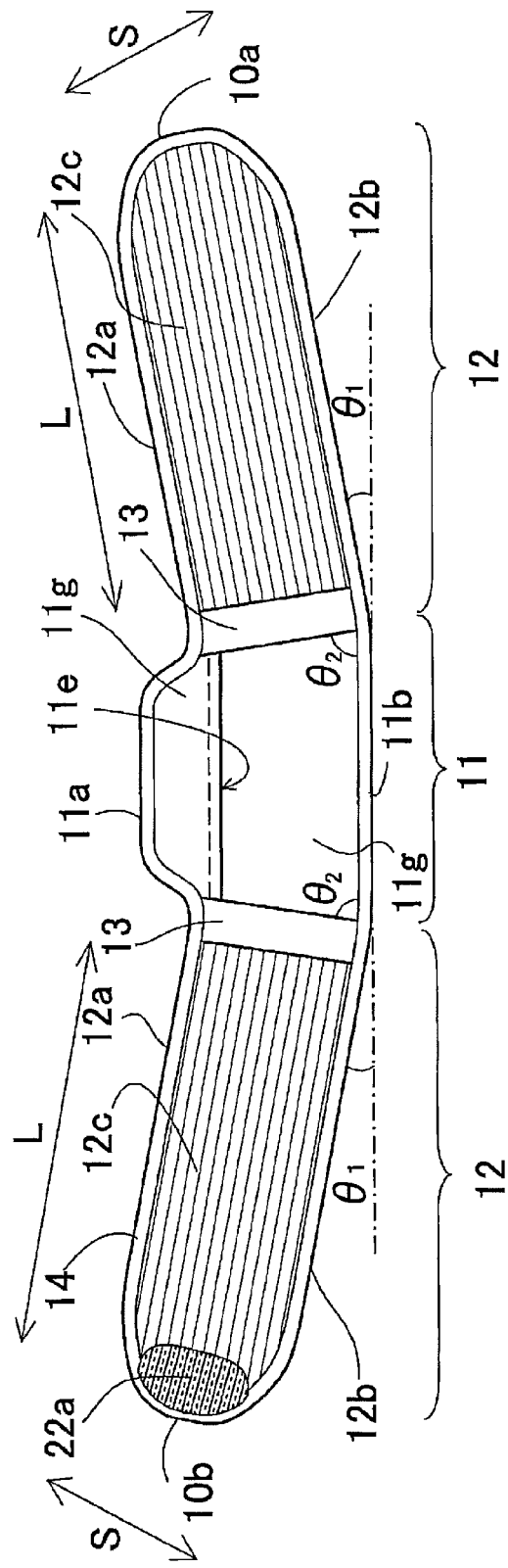
Figure 2:
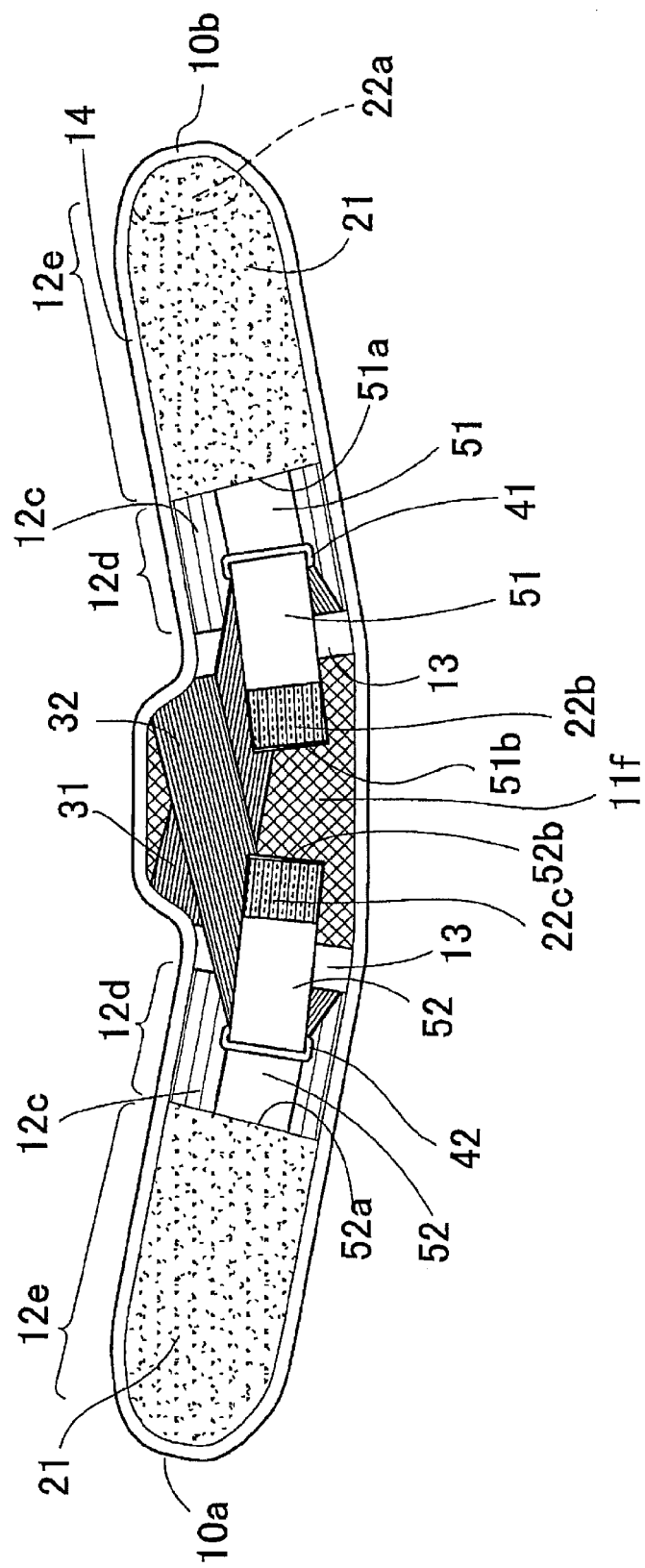
FIG. 2(a) is a diagram illustrating the front surface of the supporter in which fastening of a first adjustment band section and a first adjustment band section illustrated in FIG. 1(a) is released.
FIG. 2(b) is a front view and a rear view of a pressing section which is received in a back-contact section illustrated in FIG. 1(b)
FIG. 2(c) is a left side view and a right side view of the pressing section illustrated in FIG. 2(b).

A supporter 100 is used as a waist supporter, and roughly includes a body section 10, a fastening portion (for example, a hook-and-loop fastener 20), a pair of a first auxiliary band section 31 and a second auxiliary band section 32, a pair of a first ring 41 and a second ring 42, and a pair of a first adjustment band section 51 and a second adjustment band section 52, as illustrated in FIGS. 1 and 2.

The body section 10 is formed of a band-shaped member and includes a back-contact section 11 that is arranged substantially at the center of the band-shaped member and that comes in contact with a wearer's back region and protruding sections 12 that are arranged at ends of both sides of the back-contact section 11, in which an upper side 12a and a lower side 12b of both sides of the body section 10 are substantially parallel to each other, and that protrude upward at an angle $\theta_1$ (for example, $\theta_1=12°$ to $14°$) which is formed by a lower side 11b of the back-contact section 11 and the upper side 12a and the lower side 12b. The body section 10 is a line-symmetric planar shape having a segment connecting the midpoint of the upper side 11a of the back-contact section 11 and the midpoint of the lower side 11b thereof as a symmetric axis and brings the lining surface (see FIG. 1(b)) into contact with a wearer's lumbar region to surround the lumbar region.

The back-contact section 11 and the protruding sections 12 are connected by pinching the front surface and the lining surface of the body section 10 with a grosgrain tape 13, which is woven using polyester yarn with a needle loom, and sewing the edge portion of the grosgrain tape 13.

In the inner layer of the grosgrain tape 13 pinching the front surface and the lining surface of the body section 10, the material of the back-contact section 11 and the material of the protruding sections 12 do not overlap with each other and are made to be flat, thereby achieving a decrease in thickness of the supporter 100, realizing a feeling of neat wearing, and making it difficult to affect outerwear even when the outerwear is worn on the supporter 100.

Particularly, by sewing the materials of the back-contact section 11 and the protruding sections 12 with a zigzag chain stitch (zigzag stitch), it is possible to keep the thickness of the supporter 100 small and to realize durability against vigorous use of the supporter 100.

In the body section 10 according to this embodiment, the edges (cut edges) of the back-contact section 11, the protruding sections 12, and the grosgrain tape 13 are inserted into a binder tape 14 and are sewed (with a binder), but raveling prevention or decoration in the cut edges of the back-contact section 11, the protruding sections 12, and the grosgrain tape 13 may be made by edge sewing, bias frame sewing, or the like. Particularly, in the binder of the cut edges of the protruding sections 12, since the binder tape 14 is sewed by zigzag chain stitch (zigzag stitch), neighboring seams are not dense and thus stretchability in the longitudinal direction L of the protruding sections 12 is not suppressed, which is preferable.

The back-contact section 11 according to this embodiment has a planar shape of a substantially isosceles trapezoid in which the corners at both ends of the upper side 11a (upper bottom) are rounded so as to continuously connect the upper side 11a and the upper side 12a of the protruding sections 12 in a substantially S-shaped, and the angle $\theta_2$ formed by the non-parallel opposite sides (the left side 11c and the right side 11d) and the lower side 11b (lower bottom) of the back-contact section 11 is $90°-\theta_1$ (for example, $\theta_2=76°$ to $78°$ in case of $\theta_1=12°$ to $14°$.

The back-contact section 11 according to this embodiment has a bag-like body having an opening 11e on the lining surface and has a configuration in which a pressing section 60 formed of a hard plate-shaped member having high rigidity and not having stretchability as an insole can be inserted into and extracted from the bag-like body. However, when the back-contact section 11 does not have stretchability, the pressing section 60 does not need to be inserted and the back-contact section does not need to be a bag-like body.

It is preferable that the back-contact section 11 is formed as a bag-like body so as to be able to insert and extract the pressing section 60, so that the hardness of the back-contact section 11 can be adjusted by existence or non-existence of the pressing section 60, changing the material of the pressing section 60, or the like and the supporter 100 can be washed to be sanitary by extracting the pressing section 60 from the back-contact section 11.

It is also preferable that the back-contact section 11 be formed as a bag-like body, so that an accessory based on a wearer's request can be received to improve convenience of the supporter 100 and, for example, a pocket heater can be received to enhance heat-retaining ability of the supporter 100.

Since the back-contact section 11 according to this embodiment uses as an outer fabric a mesh material (raschel mesh 11f) knitted using nylon yarn with a double raschel warp knitting machine, foreign materials such as fiber waste gathering in the bag-like body can be discharged externally from stitches, which is sanitary, and breathability in the back-contact section 11 can be improved. In the back-contact section 11 according to this embodiment, resin treatment is performed in finishing the raschel mesh 11f to increase hardness of the warp-knitted fabric and to enhance a supporting force of the supporter 100 against a wearer's back region.

The back-contact section 11 according to this embodiment provides a satisfactory sense of touch and is soft against the wearer's back region by using as lining fabric crochet-knitted material (crochet-knitted fabric 11g) knitted using polyurethane yarn and polyester yarn having heat resistance with a crochet warp knitting machine, and can prevent an accessory such as a pocket heater received in the bag-like body from falling from the opening 11e by causing two sheets of crochet-knitted fabric 11g to overlap at the opening 11e.

The back-contact section 11 according to this embodiment uses warp-knitted fabric not subjected to resin treatment as lining fabric. Accordingly, even when the knitted fabric is cut, knitting yearn does not ravel at the cut edges, the back-contact section 11 can be processed in a free shape, and desired stretchability allowing insertion of an accessory can be given to the bag-like body.

The warp knitting machine is roughly classified into a raschel warp knitting machine for forming knits (raschel knits) which are characterized in pattern using needles in various ways and a tricot warp knitting machine for forming knits (tricot knits) which are characterized in high productivity without assuming a pattern. The raschel warp knitting machine is further classified into a double raschel warp knitting machine, a RASSERINA warp knitting machine, a lace warp knitting machine, and a crochet warp knitting machine (crochet knitting machine).

Warp knits forms stitches in the longitudinal direction (knitting direction) and couples plural warps (warping yarn) arranged in parallel to each other to form knitted fabric.

There are various types of coupling methods and representative examples thereof include a method of forming knitted fabric as a whole while entangling neighboring warps with each other or a method of forming plural independent chain stitches using individual warps, inserting another set of warps into the chain stitches, connecting several chain stitches in the transverse direction while collecting the several chain stitches, and forming knitted fabric as a whole.

Warp knits have features which are difficult to ravel, stretch in the transverse direction (direction perpendicular to the knitting direction) is small, productivity thereof is high, the knitting width is large, and the like.

The pressing section 60 according to this embodiment employs a resin panel formed of polypropylene (PP) with a melting point of 150 C to 160 C having heat resistance better than that of a polyethylene material with a melting point of 105 C to 120 C. Accordingly, when a pocket heater is received in the back-contact section 11, it is possible to suppress deformation due to radiation of heat from the pocket heater.

The pressing section 60 according to this embodiment has a planar shape of a substantial isosceles trapezoid corresponding to the planar shape of the back-contact section 11 as illustrated in FIG. 2(b) and has a shape in which four corners thereof are rounded and a concave portion 63 is formed at the centers of an upper bottom 61 and a lower bottom 62. Accordingly, the pressing section 60 can be easily twisted with respect to a segment connecting the midpoint of the upper bottom 61 and the midpoint of the lower bottom 62, generates resilience to the twist, and assists a pivoting foot in the wearer's motion to smooth the wearer's walk. In case of a resin panel having the concave portions 63 not formed in the pressing section 60, when the pressing section 60 is twisted with respect to the segment connecting the midpoint of the upper bottom 61 and the midpoint of the lower bottom 62, the central portion of the upper bottom 61 protrudes the highest and thus the protruding portion of the pressing section 60 comes in contact with the wearer's back region to cause pain. As a result, it is preferable that the concave portion 63 be formed at the center of the upper bottom 61.

The protruding sections 12 according to this embodiment include regions (hereinafter, referred to as stretchable portion 12d) being arranged on both sides of the back-contact section 11 and having stretchability and regions (hereinafter, referred to as non-stretchable portion 12e) being arranged to adjacent to the stretchable portion 12d and not having stretchability. A case where a non-stretchable member is arranged on a substrate having stretchability will be described below as an aspect of the present invention.

Each protruding section 12 is a knitted fabric having a power net fabric 12c, which is knitted with a needle loom and is woven using a nylon monofilament (single fiber) so as to prevent folding of the fabric in addition to polyurethane yarn and polyester yarn, as a substrate, having stretchability in the longitudinal direction L, and having suppressed stretchability in the short-length direction S.

When normal monofilament yarn (for example, 600 denier per one yarn) is used for the protruding sections 12, a piece of monofilament yarn is thick and is a warp such as a wire, and thus the tip of the monofilament yarn may protrude from the cut edge and may thrust the wearer. Accordingly, in the protruding sections 12 according to this embodiment, desired hardness and breathability are maintained using a set of yarn (for example, 10 pieces) of monofilament yarn of a low count (for example, 50 denier per one yarn), and the tips of monofilament yarn are prevented from protruding from the cut edges. Even when the monofilaments protrude, the thickness of one monofilament yarn is small and thus the tips of the monofilament yarns do not thrust the wearer, thereby reducing stimulus of the wearer's skin.

In the protruding sections 12 according to this embodiment, resin treatment having a high resin concentration is performed on finishing of the protruding sections 12 to further raise the fabric hardness, thereby enhancing the supporting force of the supporter 100 against the wearer's front abdomen and lateral abdomen. In addition, since the fabric has a mesh structure, breathability is excellent.

The fastening portion is formed on the front surface of both ends (the left end 10a and the right end 10b) of the body section 10 and the lining surface of the left end 10a or the right end 10b of the body section 10 and fastens different surfaces of the body section 10. In this embodiment, the supporter 100 uses a hook-and-loop fastener 20 as the fastening portion, but the fastening portion is not limited to the hook-and-loop fastener 20 as long as both end portions of the body section 10 can be fastened. For example, a button, a dot button, a snap, a hook, a buckle, a fastener (a zipper or a chuck), a front hook, or a spindle stopper may be used.

The body section 10 according to this embodiment, loops 21 of the hook-and-loop fastener 20 are arranged in both end portions (the left end 10a and the right end 10b) on the front surface illustrated in FIG. 1(a) and hooks 22a of the hook-and-loop fastener 20 are arranged in the right end 10b side on the lining surface illustrated in FIG. 1(b). The hooks 22a may be arranged on the front surface and the loops 21 may be arranged on the lining surface, or the side on which the hooks 22a on the lining surface may be changed from the right end 10b side to the left end 10a side.

In the supporter 100 according to this embodiment, edges (cut edges) of the loops 21 of the hook-and-loop fastener 20 along with the protruding section 12 are pinched by the binder tape 14 and are sewed.

In the supporter 100 according to this embodiment, one end of the binder tape 14 is arranged on the right end 10b of the body section 10, the other end of the binder tape 14 surrounding the body section 10 is arranged on the lining surface side of the body section 10, the other end of the binder tape 14 is pinched between the hooks 22a of the hook-and-loop fastener 20 and the protruding section 12 (the power net fabric 12c), and the other end of the binder tape 14 is sewed at the same time as sewing the hooks 22a to the protruding section 12 (the power net fabric 12c). By employing this configuration, it is possible to simplify the process of producing the supporter 100 and to prevent the other end of the binder tape 14 from protruding from the surface of the supporter 100, thereby not damaging the beauty of the supporter 100.

In the supporter 100 according to this embodiment, since the hook-and-loop fasteners 20 (the loops 21) at both ends of the body section 10 do not have stretchability, only the regions between the back-contact section 11 (the grosgrain tapes 13) and the loops 21, those are arranged at both sides of the back-contact section 11 (the grosgrain tapes 13) across the body section 10 (the protruding sections 12) between the upper side 12a and the lower side 12b thereof, have stretchability in the protruding sections 12. That is, in the protruding sections 12, the regions having the loops 21 arranged therein correspond to the non-stretchable portions 12e and the regions (regions between the grosgrain tapes 13 and the loops 21) not having the loops 21 arranged therein correspond to the stretchable portions 12d. The stretchable portions 12d of the protruding sections 12 have stretchability higher than stretchability of the first auxiliary band section 31 and the second auxiliary band section 32 to be described later.

A pair of auxiliary band sections according to this embodiment includes two band-shaped members (the first auxiliary band section 31 and the second auxiliary band section 32) having stretchability in the longitudinal direction and is fixed so that the two band-shaped members cross each other on the back-contact section 11.

The first auxiliary band section 31 is formed of a band-shaped member having stretchability in the longitudinal direction of the first auxiliary band section 31. One end 31a of the band-shaped member is fixed to one end of the upper side 11a (for example, the top end of the left side 11c) of the back-contact section 11 on the front surface of the body section 10, and the other end 31b of the band-shaped member is fixed to the bottom end of one lateral side (for example, the right side 11d) of the back-contact section 11 on the front surface of the body section 10.

As illustrated in FIG. 1(a), a part of one end 31a of the first auxiliary band section 31 according to this embodiment is pinched and sewed between the back-contact section 11 (the raschel mesh 110 and the grosgrain tape 13 at one end of the upper side 11a (the top end of the left side 11c) of the back-contact section 11, and the other part is pinched and sewed in the binder tape 14 along with the back-contact section 11 (the raschel mesh 110. As illustrated in FIG. 1(a), the other end 31b of the first auxiliary band section 31 according to this embodiment is pinched and sewed between the protruding section 12 (the power net fabric 12c) and the grosgrain tape 13 at the bottom end of one lateral side (the right side 11d) of the back-contact section 11.

The second auxiliary band section 32 is formed of a band-shaped member having stretchability in the longitudinal direction of the second auxiliary band section 32. One end 32a of the band-shaped member is fixed to the other end of the upper side 11a (for example, the top end of the right side 11d) of the back-contact section 11 on the front surface of the body section 10, and the other end 32b of the band-shaped member is fixed to the bottom end of the other lateral side (for example, the left side 11c) of the back-contact section 11 on the front surface of the body section 10. The second auxiliary band section forms a pair with the first auxiliary band section 31.

Particularly, since the planar shape of the back-contact section 11 is substantially isosceles trapezoidal and the length of the upper side 11a (upper bottom) of the back-contact section 11 is smaller than the length of the lower side 11b (lower bottom), the first auxiliary band section 31 and the second auxiliary band section 32 cross each other in the vicinity of the upper side 11a of the back-contact section 11 (the raschel mesh 110. The configuration in which the second auxiliary band section 32 goes over the first auxiliary band section 31 is illustrated as the cross section of the first auxiliary band section 31 and the second auxiliary band section 32 in FIGS. 1(a), 1(e), 1(f), 2(a), 5(b), 5(c), 6(b), and 6(c), but a configuration in which the first auxiliary band section 31 goes over the second auxiliary band section 32 may be employed.

As illustrated in FIG. 1(a), a part of one end 32a of the second auxiliary band section 32 according to this embodiment is pinched and sewed between the back-contact section 11 (the raschel mesh 110 and the grosgrain tape 13 at the other end of the upper side 11a (the top end of the right side 11d) of the back-contact section 11, and the other part is pinched and sewed in the binder tape 14 along with the back-contact section 11 (the raschel mesh 110. As illustrated in FIG. 1(a), the other end 32b of the second auxiliary band section 32 according to this embodiment is pinched and sewed between the protruding section 12 (the power net fabric 12c) and the grosgrain tape 13 at the bottom end of the other lateral side (the left side 11c) of the back-contact section 11.

The first auxiliary band section 31 and the second auxiliary band section 32 according to this embodiment are woven rubber woven using polyurethane yarn and polyester yarn with a needle loom. Due to the use of polyurethane as a material of an elastic fiber, they are excellent in durability (heat resistance) and an allergic response (hypersensitive reaction) which is caused when crude rubber is used as the material of the elastic fiber is reduced that is good for the wearer's skin.

The first ring 41 has an annular shape and is arranged to be slidable between one end 31a and the other end 32b of the first auxiliary band section 31.

The second ring 42 has an annular shape and is arranged to be slidable between one end 32a and the other end 32b of the second auxiliary band section 32. The second ring forms a pair with the first ring 41.

The first ring 41 and the second ring 42 according to this embodiment are flat rings molded by a metallic molding machine and use polyacetal as the material thereof, whereby the rings have high hardness, flexibility, and heat resistance.

A pair of adjustment band sections according to this embodiment includes two band-shaped members (the first adjustment band section 51 and the second adjustment band section 52) having stretchability.

The first adjustment band section 51 is formed of a band-shaped member which is loosely inserted into the first ring 41 and which has stretchability lower than stretchability of the first auxiliary band section 31. One end 51a of the band-shaped member is fixed to the non-stretchable portion 12e of the protruding section 12 on the right end 10b side of the body section 10 on the front surface of the body section 10 and the other end 51b of the band-shaped member can be fastened to a region other than the stretchable portion 12d of the protruding section 12 on the right end 10b side of the body section 10 on the front surface of the body section 10.

The fixation position of one end 51a of the first adjustment band section 51 and the fastening position of the other end 51b thereof are located on the side closer to the right end 10b of the body section 10 with respect to the position (bent portion 31c) separated farthest from one end 31a and the other end 31b of the first auxiliary band section 31 out of a movable region of the first ring 41 bound to the first auxiliary band section 31 with a natural length in a state (see FIG. 1(a)) in which the supporter 100 is arranged flat.

In the first adjustment band section 51 according to this embodiment, a PP tape woven using polypropylene yarn and polyester yarn with a needle loom is used as a substrate, one end 51a of the first adjustment band section 51 (substrate) is pinched between the loops 21 of the hook-and-loop fastener 20 and the protruding section 12 (power net fabric 12c) substantially at the center in the short-length direction S of the protruding section 12, and one end 51a is sewed at the same time as sewing the loops 21 against the protruding section 12 (power net fabric 12c).

In the first adjustment band section 51 according to this embodiment, a fastening portion (for example, the hooks 22b of the hook-and-loop fastener 20 in FIG. 2(a)) fastened to the fastening portion on the right end 10b side of the body section 10 is arranged on the surface, which faces the fastening portion (for example, the loops 21 of the hook-and-loop fastener 20) on the right end 10b side of the body section 10, at the other end 51b of the first adjustment band section 51 (substrate) by sewing.

In this embodiment, the hooks 22b of the hook-and-loop fastener 20 is used as the fastening portion on the other end 51b side of the first adjustment band section 51 is fastened to the loops 21 of the hook-and-loop fastener 20 on the right end 10b side of the body section 10, but the present invention is not limited to this configuration.

For example, when the above-mentioned button or the like instead of the loops 21 and the hooks 22a of the hook-and-loop fastener 20 is used as the fastening portion used to fasten different surfaces of the body section 10, a hook-and-loop fastener (loops) fastened to the hooks 22b on the other end 51b side of the first adjustment band section 51 may be newly arranged in a region (for example, on the first adjustment band section 51) other than the stretchable portion 12d of the protruding section 12 on the right end 10b side of the body section 10.

The fastening portion used to fasten the different surfaces of the body section 10 and the fastening portion for fastening the other end 51b of the first adjustment band section 51 to the protruding section 12 of the body section 10 are preferably used in common, because the number of members and the number of production processes of the supporter 100 can be reduced.

The end of the substrate serving as the other end 51b of the first adjustment band section 51 according to this embodiment is folded back (returning structure) is superimposed and sewed on a folded-back portion (returning structure) of the hooks 22b of the hook-and-loop fastener 20, whereby the thickness of the other end 51b increases to prevent drop of the first adjustment band section 51 from the first ring 41 and the wearer can easily grasp the other end 51b, thereby obtaining a convenient supporter 100.

The second adjustment band section 52 is formed of a band-shaped member which is loosely inserted into the second ring 42 and which has stretchability lower than stretchability of the second auxiliary band section 32. One end 52a of the band-shaped member is fixed to the non-stretchable portion 12e of the protruding section 12 on the left end 10a side of the body section 10 on the front surface of the body section 10 and the other end 52b of the band-shaped member can be fastened to a region other than the stretchable portion 12d of the protruding section 12 on the left end 10a side of the body section 10 on the front surface of the body section 10. The second adjustment band section 52 forms a pair with the first adjustment band section 51.

The fixation position of one end 52a of the second adjustment band section 52 and the fastening position of the other end 52b thereof are located on the side closer to the left end 10a of the body section 10 with respect to the position (bent portion 32c) separated farthest from one end 32a and the other end 32b of the second auxiliary band section 32 out of a movable region of the second ring 42 bound to the second auxiliary band section 32 with a natural length in a state (see FIG. 1(a)) in which the supporter 100 is arranged flat.

In the second adjustment band section 52 according to this embodiment, a PP tape woven using polypropylene yarn and polyester yarn with a needle loom is used as a substrate, one end 52a of the second adjustment band section 52 (substrate) is pinched between the loops 21 of the hook-and-loop fastener 20 and the protruding section 12 (power net fabric 12c) substantially at the center in the short-length direction S of the protruding section 12, and one end 52a is sewed at the same time as sewing the loops 21 against the protruding section 12 (power net fabric 12c).

In the second adjustment band section 52 according to this embodiment, a fastening portion (for example, the hooks 22c of the hook-and-loop fastener 20 in FIG. 2(a)) fastened to the fastening portion on the left end 10a side of the body section 10 is arranged on the surface, which faces the fastening portion (for example, the loops 21 of the hook-and-loop fastener 20) on the left end 10a side of the body section 10, at the other end 52b of the second adjustment band section 52 (substrate) by sewing.

In this embodiment, the hooks 22c of the hook-and-loop fastener 20 is used as the fastening portion on the other end 52b side of the second adjustment band section 52 is fastened to the loops 21 of the hook-and-loop fastener 20 on the left end 10a side of the body section 10, but the present invention is not limited to this configuration.

For example, when the above-mentioned button or the like instead of the loops 21 and the hooks 22a of the hook-and-loop fastener 20 is used as the fastening portion used to fasten different surfaces of the body section 10, a hook-and-loop fastener (loops) fastened to the hooks 22c on the other end 52b side of the second adjustment band section 52 may be newly arranged in a region (for example, on the second adjustment band section 52) other than the stretchable portion 12d of the protruding section 12 on the left end 10a side of the body section 10.

The fastening portion used to fasten the different surfaces of the body section 10 and the fastening portion for fastening the other end 52b of the second adjustment band section 52 to the protruding section 12 of the body section 10 are preferably used in common, because the number of members and the number of production processes of the supporter 100 can be reduced.

The end of the substrate serving as the other end 52b of the second adjustment band section 52 according to this embodiment is folded back (returning structure), is superimposed and sewed on a folded-back portion (returning structure) of the hooks 22c of the hook-and-loop fastener 20, whereby the thickness of the other end 52b increases to prevent drop of the second adjustment band section 52 from the second ring 42 and the wearer can easily grasp the other end 52b, thereby obtaining a convenient supporter 100.

Particularly, in the supporter 100 according to this embodiment, the natural length of the first auxiliary band section 31 is larger than the gap between one end of the upper side 11a (the top end of the left side 11c) of the back-contact section 11 and the bottom end of one lateral side (the right side 11d) of the back-contact section 11, and the natural length of the second auxiliary band section 32 is larger than the gap between the other end of the upper side 11a (the top end of the right side 11d) of the back-contact section 11 and the bottom end of the other lateral side (the left side 11c) of the back-contact section 11.

Accordingly, a curved portion (the bent portion 31c engaging with the first ring 41) is formed in the first auxiliary band section 31 in the state (relaxed state) where a tensile load from the first adjustment band section 51 (the first ring 41) is not applied. When the wearer wears the supporter 100 and extrudes the first adjustment band section 51 forward, the stretching direction of the first auxiliary band section 31 is specified, the initial resistance of stretching of the first auxiliary band section 31 is small, and thus the first adjustment band section 51 can be smoothly extruded.

Similarly, a curved portion (the bent portion 32c engaging with the second ring 42) is formed in the second auxiliary band section 32 in the relaxed state. When the wearer wears the supporter 100 and extrudes the second adjustment band section 52 forward, the stretching direction of the second auxiliary band section 32 is specified, the initial resistance of stretching of the second auxiliary band section 32 is small, and thus the second adjustment band section 52 can be smoothly extruded.

Figure 3:
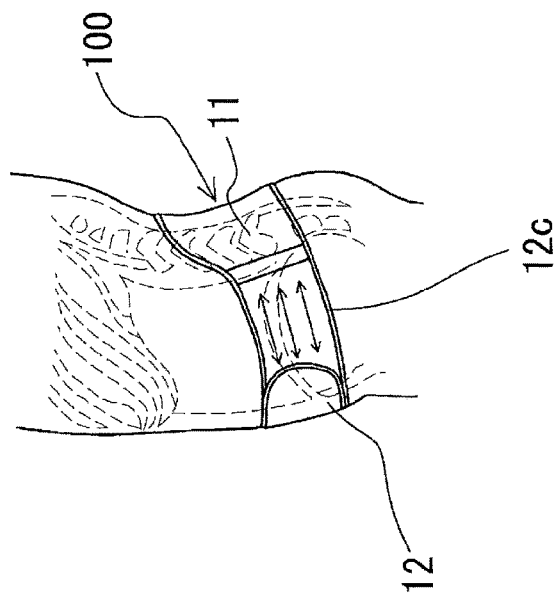
FIG. 3(a) is a skeletal diagram illustrating names of skeletons in the vicinity of a lumbar region.
FIG. 3(b) is a perspective view illustrating a wearing state of the supporter illustrated in FIG. 1 when viewed from the front-right side.
FIG. 3(c) is a perspective view illustrating the wearing state of the supporter illustrated in FIG. 1 when viewed from the rear-right side.
FIG. 3(d) is a right side view illustrating the wearing state of the supporter illustrated in FIG. 1.
FIG. 3(e) is a front view illustrating a V-shaped wearing state of the supporter illustrated in FIG. 1.
Figure 3:
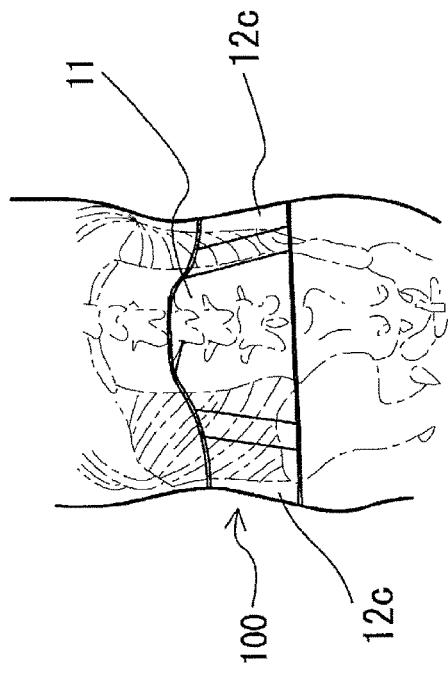
Figure 3:
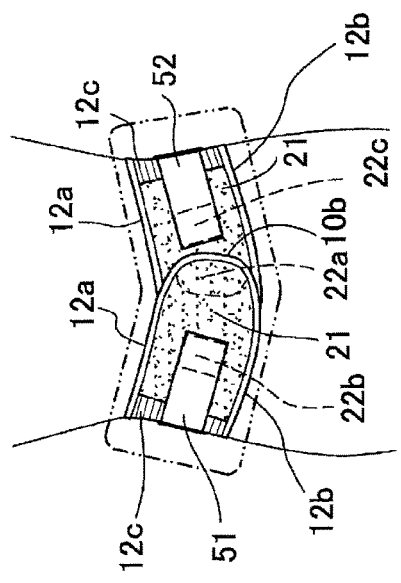
Figure 4:
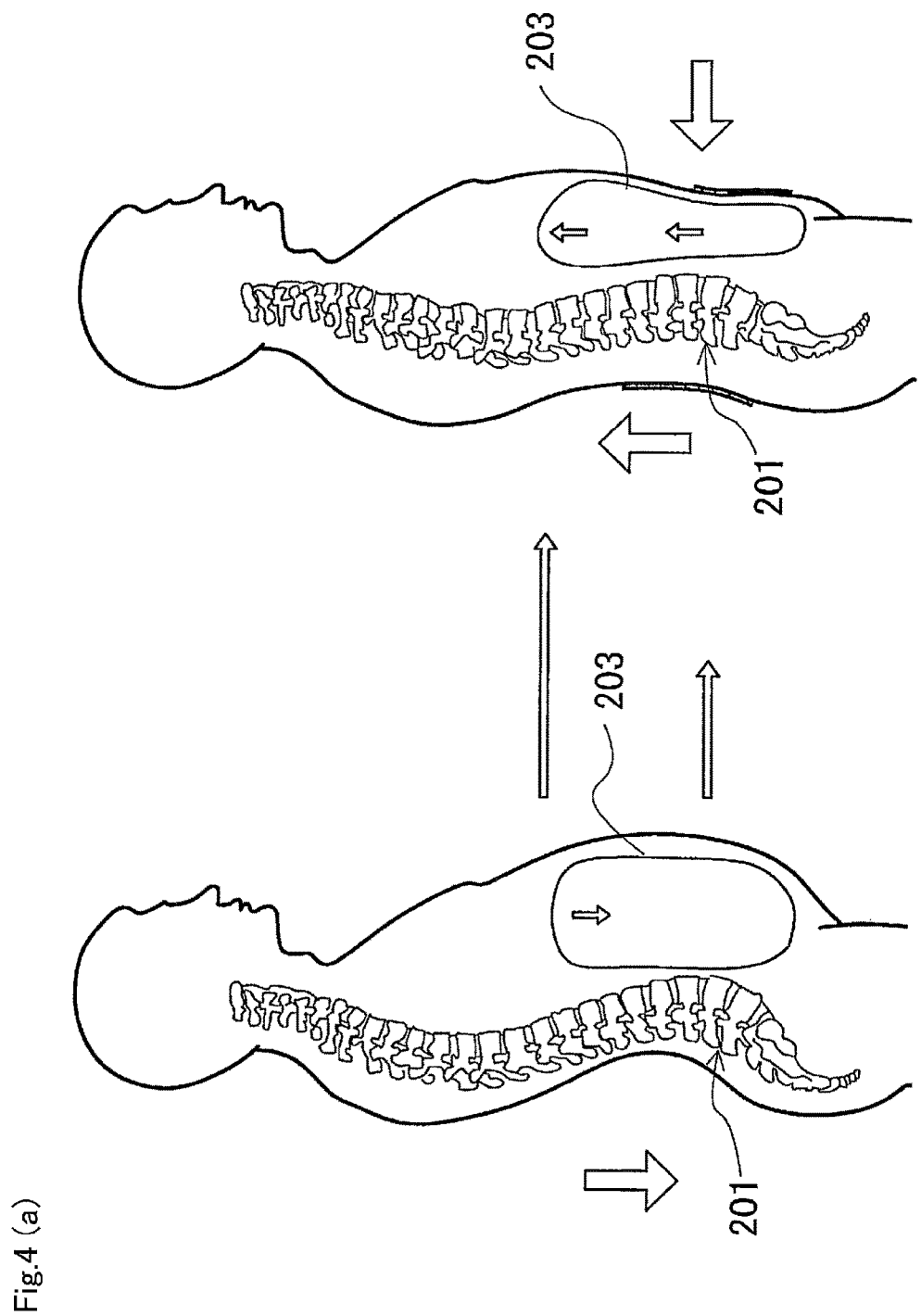
FIG. 4(a) is a diagram illustrating an intraperitoneal pressure increasing effect and FIG. 4(b) is a diagram illustrating prevention of retroflexion.
Figure 4:
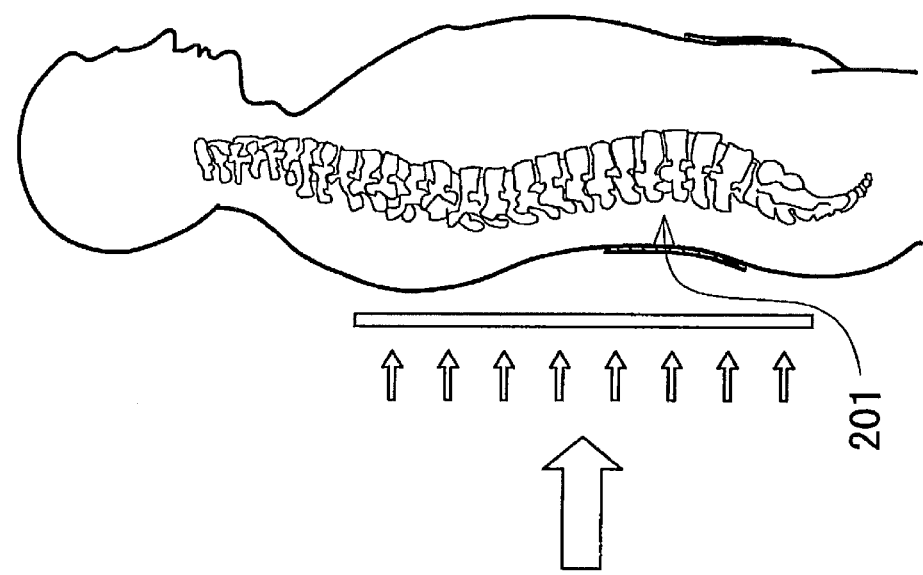
Figure 4:
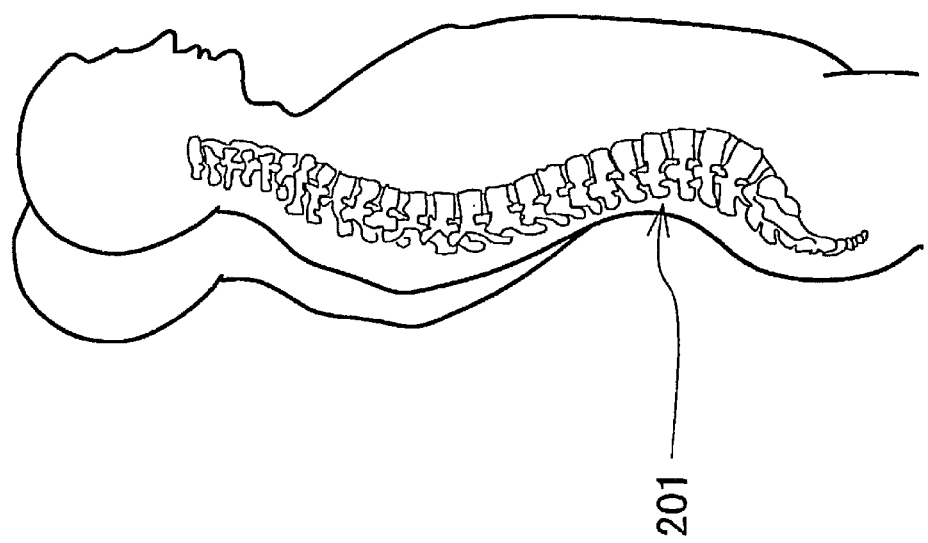

The operational advantages based on the body section 10 of the supporter 100 and the fastening portion (hook-and-loop fastener 20) will be described below with reference to FIGS. 3 and 4. In FIGS. 3(b) to 3(d), the first auxiliary band section 31, the second auxiliary band section 32, the first ring 41, the second ring 42, the first adjustment band section 51, and the second adjustment band section 52 are not illustrated, and the stretching direction of the body section 10 (protruding section 12) of the supporter 100 is indicated by an arrow.

Here, as illustrated in FIG. 3(a), a waist includes a lumbar vertebrae 201 having five bones superimposed and a pelvis 202. The lumbar vertebrae 201 is supported by an abdominal muscle group such as a lateral abdominal muscle and a posterior abdominal muscle located in the abdomen and a back muscle group such as a superficial back muscle and a deep back muscle located in the back region.

Accordingly, in order to alleviate lumbar pain, it is effective that the waist is kept from the outside and the abdomen is pushed up from the lower side to raise the pressure of the abdominal cavity 203 and thus to support the lumbar vertebrae 201 as illustrated in FIG. 4(a) (intraperitoneal pressure increasing effect).

Keeping of a correct posture is to stabilize the lumbar vertebrae 201 and it is possible to reduce a burden to the lumbar vertebrae 201 by preventing movement of retroflexion which applies the largest burden on the lumbar region as illustrated in FIG. 4(b) (prevention of retroflexion).

By applying a pressure to an ilium 205 from both side surfaces to tighten a sacroiliac joint 206, it is possible to suppress fluctuation of a sacrum 204 which is a base of the lumbar vertebrae 201 (stabilization of the sacroiliac joint).

Therefore, the supporter 100 according to this embodiment has a planar shape of a substantial isosceles trapezoid in which the corners at both ends of the upper side 11a (upper bottom) of the back-contact section 11 are rounded, and the longitudinal direction L of the right and left protruding sections 12 is substantially perpendicular to the right side 11d and the left side 11c of the back-contact section 11. Accordingly, in the state where the wearer wears the supporter 100, as illustrated in FIG. 3, the back-contact section 11 is located in a part corresponding to the lumbar vertebrae 201 in the wearer's back region and the protruding section 12 (upper side 12a) is located below a part corresponding to a rib (twelfth rib) 207 in the front abdomen of the wearer and below (around the ilium 205) a part corresponding to the rib (twelfth rib) 207 in the lateral abdomen of the wearer.

That is, since the protruding sections 12 of the body section 10 can pressurize the abdominal cavity 203 without being hindered by the rib 207 while the back-contact section 11 of the body section 10 supports the wearer's lumbar vertebrae 201, it is possible to provide an intraperitoneal pressure increasing effect to the wearer and to prevent retroflexion of the lumbar region. In the supporter 100, since the protruding section 12 of the body section 10 is located below the part corresponding to the rib (twelfth rib) 207 in the front abdomen of the wearer and do not pressurize the rib 207, it is possible to easily carry out anteflexion (there is no interference with daily motions) without interfering with the movement of anteflexion of the lumbar region. Since the supporter does not pressurize the wearer's stomach, there is no feeling of pressing on the stomach and the feeling of wearing the supporter 100 is good.

Particularly, the supporter 100 employs the protruding sections 12 having stretchability in the longitudinal direction L given thereto and having stretchability in the short-length direction S suppressed. Accordingly, as illustrated in FIGS. 3(b) and 3(d), a stretching force of the body section 10 acts in an oblique upward direction (the direction of arrow) from the front abdomen to the lateral abdomen, the abdomen is pushed up from the lower side, internal organs of the ribs 207 is further pushed up, the pressure applied to the internal organs is transmitted to the backbone, and the backbone is supported from the inner side, thereby further achieving the intraperitoneal pressure increasing effect and the prevention of retroflexion. The protruding sections 12 of the body section 10 pressurize the ilium 205 from the right and left stretchable portions 12d, and the sacroiliac joint 206 is tightened to stabilize the sacroiliac joint 206.

When a wearer wears the supporter 100, both ends (the left end 10a and the right end 10b) of the body section 10 are located in the front abdomen of the wearer and thus both ends of the body section 10 pressurize the front abdomen of the wearer. Since the hook-and-loop fastener 20 (loops 21) not having stretchability is arranged at both ends of the body section 10 (the protruding sections 12), it is possible to prevent the pressure applied to the abdominal cavity 203 of the wearer from being distributed in the longitudinal direction L of the protruding sections 12 by the stretching of the protruding sections 12 and to concentrate the pressure on the abdominal cavity 203, thereby further enhancing the intraperitoneal pressure increasing effect.

Particularly, the supporter 100 according to this embodiment can effectively lift up the lower abdomen of the wearer to further enhance the intraperitoneal pressure increasing effect, as illustrated in FIG. 3(e), by wearing the supporter so that the upper side 12a (the lower side 12b) of the protruding section 12 on the left end 10a side of the body section 10 and the upper side 12a (the lower side 12b) of the protruding section 12 on the right end 10b side of the body section 10 form a substantially V shape (V-shaped wearing state).

The operational advantages when the supporter 100 includes the first auxiliary band section 31, the second auxiliary band section 32, the first ring 41, the second ring 42, the first adjustment band section 51, and the second adjustment band section 52 in addition to the body section 10 and the fastening portion (hook-and-loop fastener 20) will be described with reference to FIGS. 5 and 6 along with the wearing order of the supporter 100.

First, a wearer inserts the pressing section 60 into the back-contact section 11 through the opening 11e, releases the fastening of the loops 21 on the right end 10b side of the body section 10 (the protruding section 12) and the hooks 22b of the first adjustment band section 51, and releases the fastening the loops 21 on the left end 10a side of the body section 10 (the protruding section 12) and the hooks 22c of the second adjustment band section 52.

Figure 5:
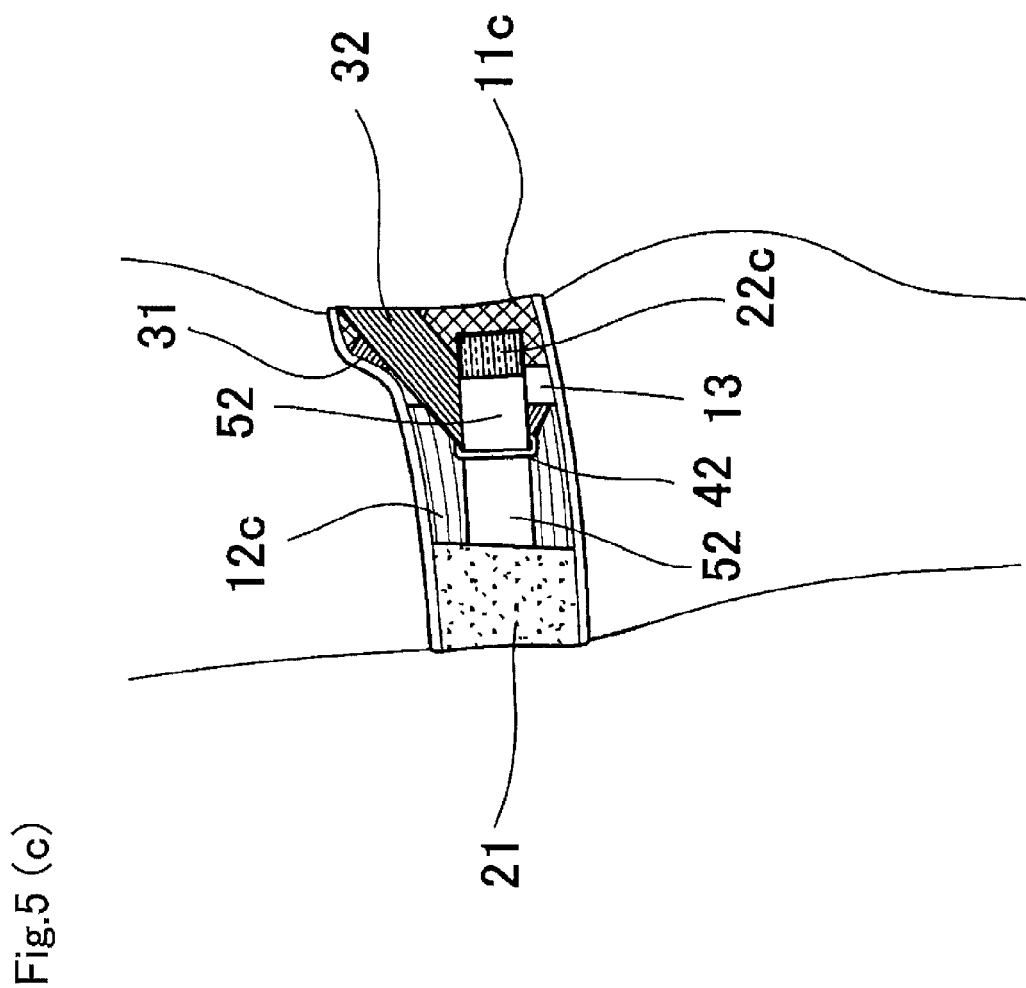
FIG. 5(a) is a front view illustrating a wearing method of the supporter illustrated in FIG. 1.
FIG. 5(b) is a rear view illustrating the wearing method of the supporter illustrated in FIG. 1.
FIG. 5(c) is a right side view illustrating the wearing method of the supporter illustrated in FIG. 1.

As illustrated in FIG. 5, the wearer causes the back-contact section 11 of the body section 10 to support the wearer's back region (the vicinity of the fifth lumbar vertebrae), winds the body section 10 onto the wearer's lumbar region from the left end 10a side in a state where the stretchable portions 12d of the protruding sections 12 are stretched up to the stretching limit in the longitudinal direction L, winds the body section on the wearer's lumbar region from the right end 10b side, and fastens the hooks 22a on the right end 10b side of the body section 10 (the protruding section 12) to the loops 21 on the left end 10a side of the body section 10 (the protruding section 12).

In this case, since the first auxiliary band section 31 and the second auxiliary band section 32 does not receive the tensile load from the first adjustment band section 51 (the first ring 41) and the second adjustment band section 52 (the second ring 42), they are in the relaxed state (natural length) and do not pressurize the back-contact section 11.

Then, the wearer grasps the other end 51b of the first adjustment band section 51 and the other end 52b of the second adjustment band section 52 with the respective hands and extrudes the first adjustment band section 51 and the second adjustment band section 52 forward.

In this case, the first ring 41 slides over the first adjustment band section 51 to follow the movement of the other end 51b of the first adjustment band section 51 and moves forward due to the stretchability of the first auxiliary band section 31, and the first auxiliary band section 31 is stretched to follow the movement of the first ring 41.

Similarly, the second ring 42 slides over the second adjustment band section 52 to follow the movement of the other end 52b of the second adjustment band section 52 and moves forward due to the stretchability of the second auxiliary band section 32, and the second auxiliary band section 32 is stretched to follow the movement of the second ring 42.

A force is applied to the stretchable portions 12d of the protruding sections 12 in the direction in which the gap between the back-contact section 11 (the grosgrain tape 13) and the hook-and-loop fastener 20 (the loops 21) decreases by the first auxiliary band section 31, the first ring 41, the first adjustment band section 51, the second auxiliary band section 32, the second ring 42, and the second adjustment band section 52.

However, in the supporter 100 according to this embodiment, the hooks 22a of the right end 10b side of the body section 10 are fastened to the loops 21 on the left end 10a side of the body section 10 in the state where the stretchable portions 12d having stretchability higher than the stretchability of the first auxiliary band section 31 and the second auxiliary band section 32 are stretched up to the stretching limit in the longitudinal direction L. Accordingly, before the stretched stretchable portions 12d start the contraction, the first auxiliary band section 31 and the second auxiliary band section 32 start the stretching, the gap between the back-contact section 11 and the loops 21 can be reduced by the stretching of the stretchable portions 12d and thus formation of wrinkles in the stretchable portions 12d can be suppressed.

When the degree of stretching of the woven rubber between the bent portion 31c and the other end 31b reaches a limit, the first auxiliary band section 31 moves the first ring 41 upward, the woven rubber between the bent portion 31c and one end 31a is sent to the other end 31b side, and the woven rubber on the one end 31a side and the woven rubber on the other end 31b side complement each other.

Similarly, when the degree of stretching of the woven rubber between the bent portion 32c and the other end 32b reaches a limit, the second auxiliary band section 32 moves the second ring 42 upward, the woven rubber between the bent portion 32c and the one end 32a is sent to the other end 32b side, and the woven rubber on the one end 32a side and the woven rubber on the other end 32b side complement each other.

Figure 6:
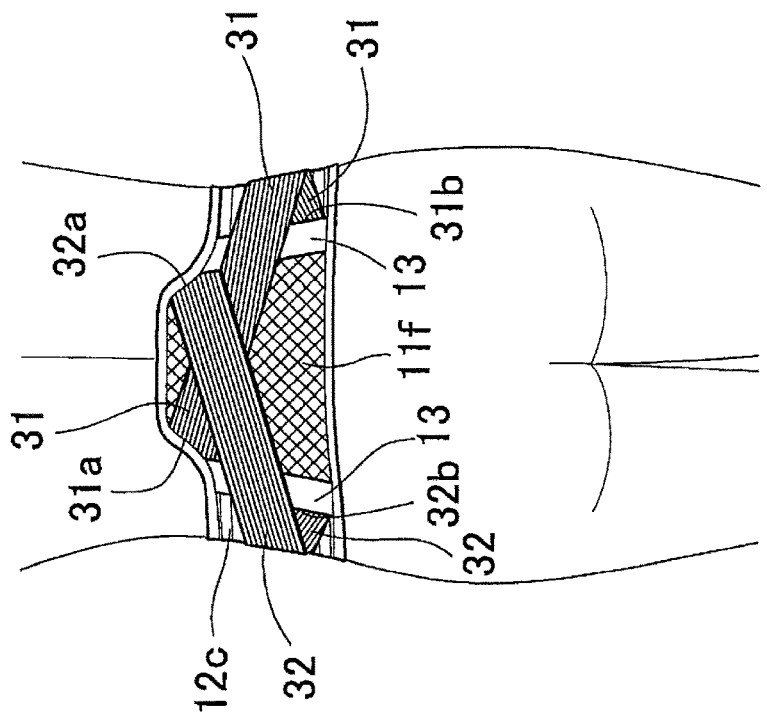
FIG. 6(a) is a front view illustrating a next step of the wearing method of the supporter illustrated in FIG. 5(a)
FIG. 6(b) is a rear view illustrating a next step of the wearing method of the supporter illustrated in FIG. 5(b)
FIG. 6(c) is a right side view illustrating a next step of the wearing method of the supporter illustrated in FIG. 5(c).
Figure 6:
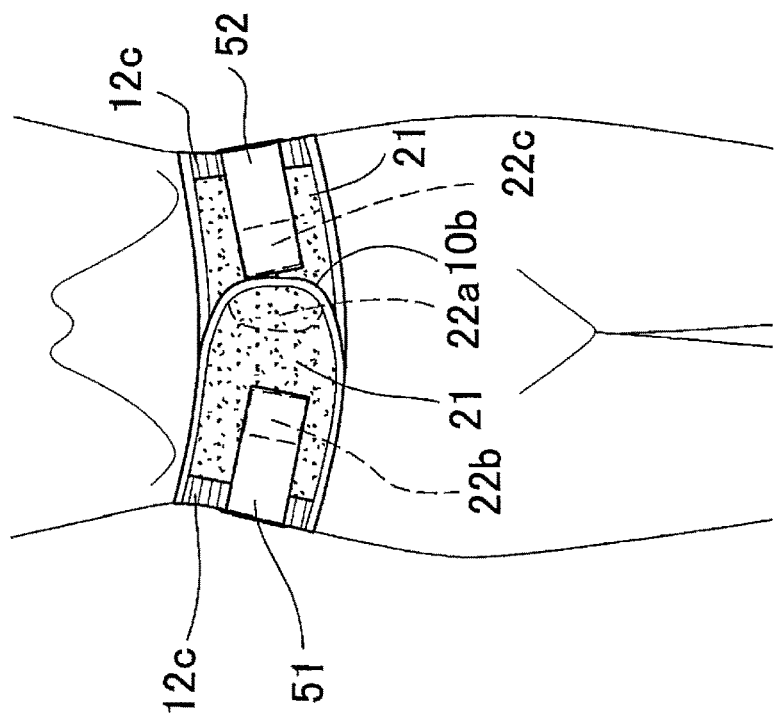
Figure 6:
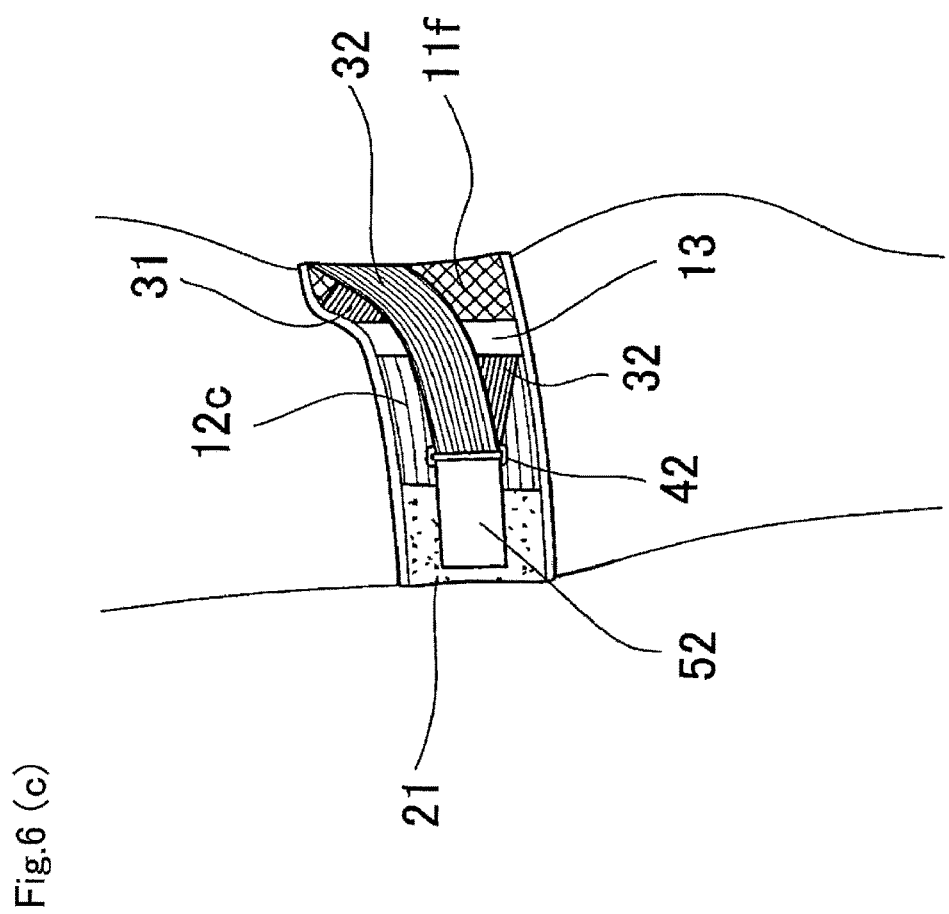

As illustrated in FIG. 6, the wearer fastens the hooks 22b of the first adjustment band section 51 to the loops 21 on the right end 10b side of the body section 10 (the protruding section 12) and fastens the hooks 22c of the second adjustment band section 52 to the loops 21 on the left end 10a side of the body section 10 (the protruding section 12), in the step where a desired feeling of fastening to the lumbar region is obtained.

In this case, since the first auxiliary band section 31 and the second auxiliary band section 32 receives the tensile load from the first adjustment band section 51 (the first ring 41)

and the second adjustment band section 52 (the second ring 42), they are in the tension state. The first auxiliary band section 31 and the second auxiliary band section 32 pressurize the back-contact section 11 as a whole to support the wearer's waist as a whole by the use of the back-contact section 11, by crossing each other over the back-contact section 11 due to three-point supporting of one end (31*a*, 32*a*), the other end (31*b*, 32*b*), and the bent portion (31*c*, 32*c*).

Particularly, the supporter 100 according to this embodiment, as illustrated in FIG. 1(*a*), the other end 31*b* of the first auxiliary band section 31 is located on the right end 10*b* side of the body section 10 with respect to the one end 32*a* of the second auxiliary band section 32, and the other end 32*b* of the second auxiliary band section 32 is located on the left end 10*a* side of the body section 10 with respect to the one end 31*a* of the first auxiliary band section 31. In this configuration, the first auxiliary band section 31 and the second auxiliary band section 32 cross each other above the center of the back-contact section 11, that is, in the vicinity of the upper side 11*a* of the back-contact section 11 (cross-taping structure).

The vicinity of the upper side 11*a* of the back-contact section 11 is an important region as a support receiving a pressing force applied in an oblique upward direction onto the wearer's abdominal cavity 203 from the hook-and-loop fastener 20 (the loops 21) at both ends (the left end 10*a* and the right end 10*b*) of the body section 10.

Accordingly, the first auxiliary band section 31 and the second auxiliary band section 32 cross each other in the vicinity of the upper side 11*a* of the back-contact section 11, the first auxiliary band section 31 and the second auxiliary band section 32 are superimposed on each other in the cross section to apply a large pressing force in the oblique downward direction to the wearer's lower abdomen via the back-contact section 11, and the stability of the lumbar region by the supporter 100 is improved due to the sandwich structure of the cross section and the hook-and-loop fastener 20 (the loops 21).

On the contrary, in the vicinity of the lower side 11*b* of the back-contact section 11, the first auxiliary band section 31 and the second auxiliary band section 32 are not superimposed and the direct pressing force from the first auxiliary band section 31 and the second auxiliary band section 32 is not applied to the back-contact section 11. However, the other end 31*b* of the first auxiliary band section 31 and the other end 32*b* of the second auxiliary band section 32 apply a tensile load to the back-contact section 11, the tensile load is distributed on the surface of the back-contact section 11, and thus a small pressing force is applied to the wearer's back region in a wide range in the vicinity of the lower side 11*b* of the back-contact section 11.

That is, compared with the case where the first auxiliary band section 31 and the second auxiliary band section 32 cross each other at the center of the back-contact section 11, the supporter 100 according to this embodiment can efficiently pressurize the region (the vicinity of the fifth lumbar vertebrae) which should be most pressurized in the wearer's back region and can apply a slight pressing force to the vicinity of the lower side 11*b* of the back-contact section 11 while suppressing separation of the supporter 100 from the wearer's body surface in the vicinity of the upper side 11*a* of the back-contact section 11, thereby enhancing the fitting property of the supporter 100.

In the supporter 100 according to this embodiment, as illustrated in FIG. 1(*a*), the one end 31*a* of the first auxiliary band section 31 is fixed to the top end of the left side 11*c* of the back-contact section 11 on the front surface of the body section 10 and the other end 31*b* is fixed to the bottom end of the right side 11*d* of the back-contact section 11 on the front surface of the body section 10. In addition, the one end 32*a* of the second auxiliary band section 32 is fixed to the top end of the right side 11*d* of the back-contact section 11 on the front surface of the body section 10 and the other end 32*b* is fixed to the bottom end of the left side 11*c* of the back-contact section 11 on the front surface of the body section 10. However, the present invention is not limited to this configuration.

Figure 7:
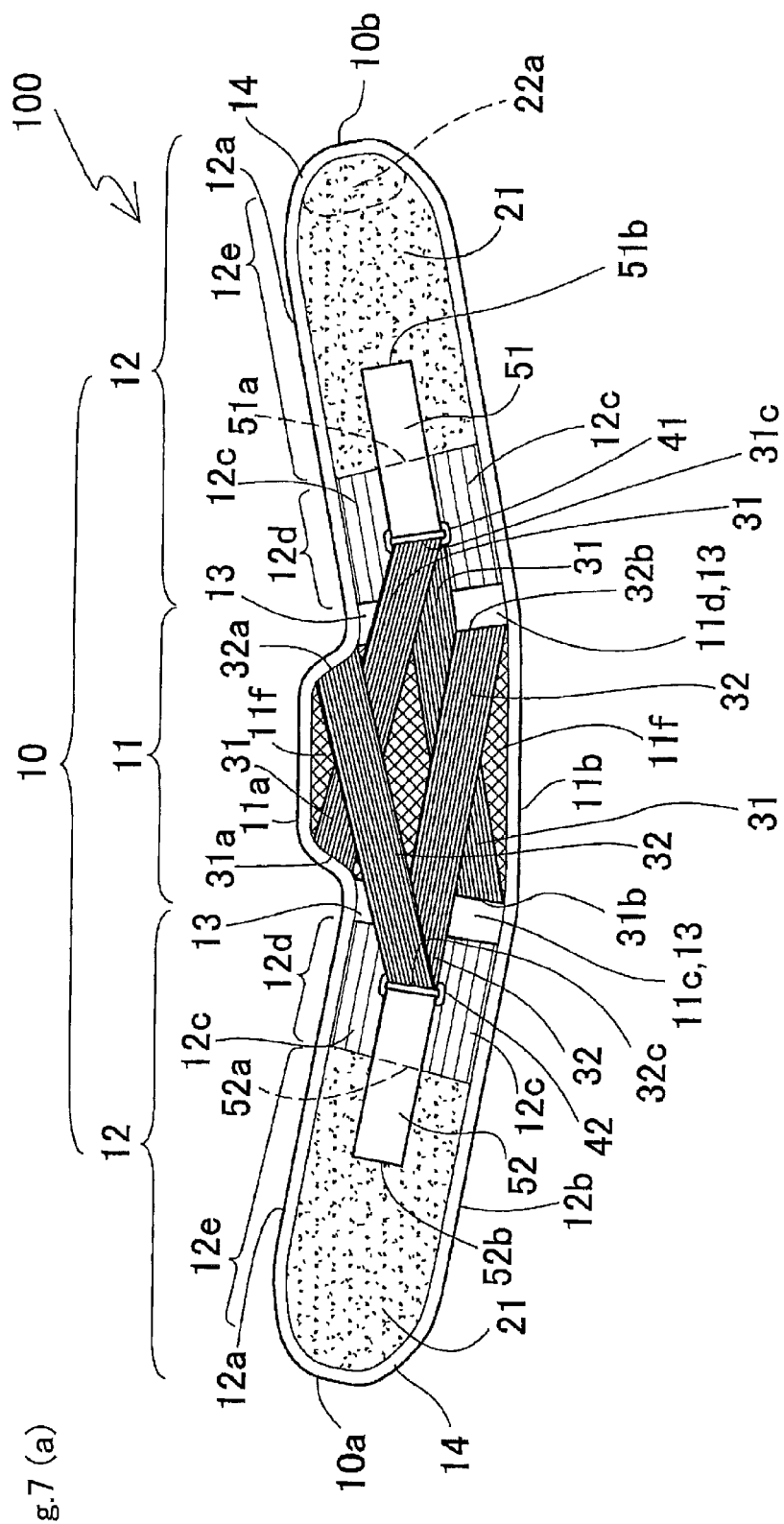
FIG. 7(a) is a diagram illustrating a front surface of another embodiment of a supporter according to a first embodiment.
FIG. 7(b) is a diagram illustrating a lining surface of the supporter illustrated in FIG. 7(a)
FIG. 7(c) is a left side view of the supporter illustrated in FIG. 7(a)
FIG. 7(d) is a right side view of the supporter illustrated in FIG. 7(a)
FIG. 7(e) is an upper side view of the supporter illustrated in FIG. 7(a)
FIG. 7(f) is a lower side view of the supporter illustrated in FIG. 7(a).
Figure 7:
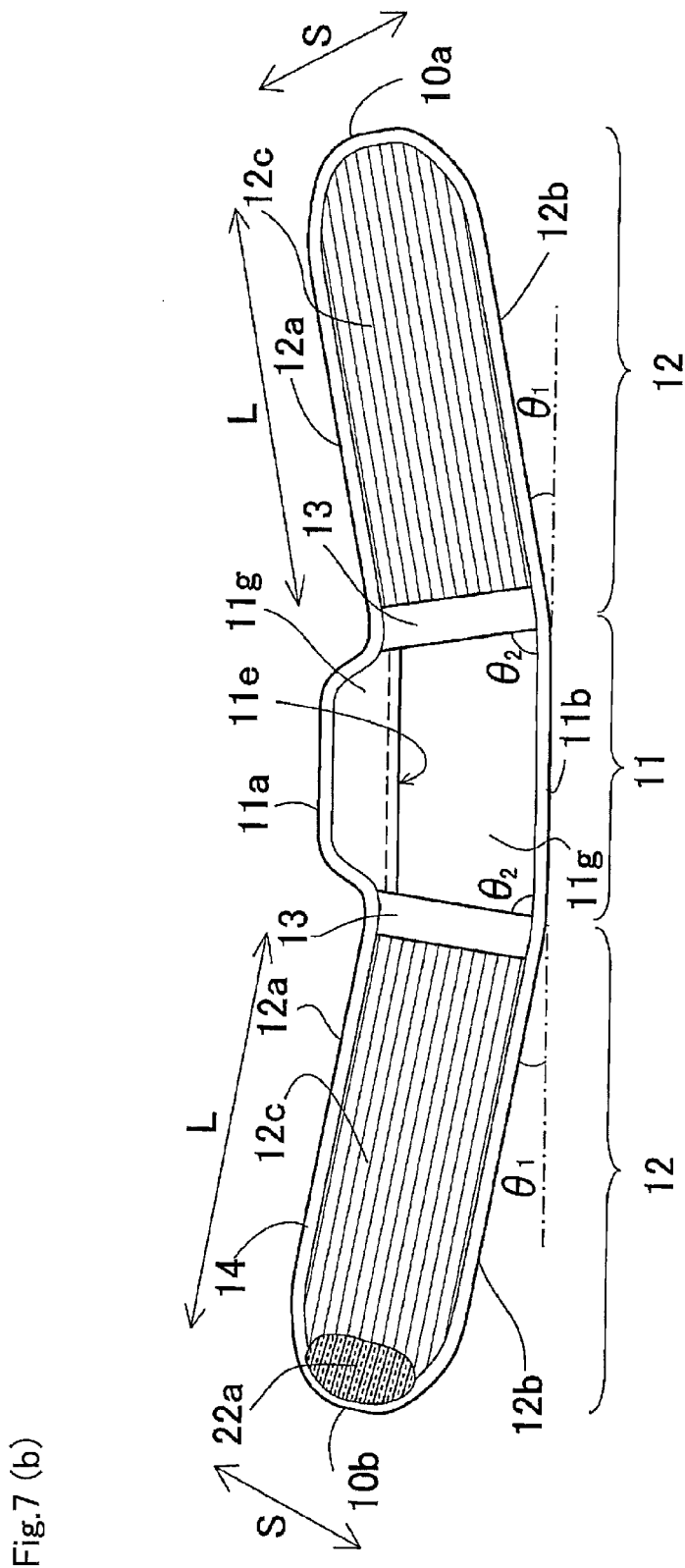
Figure 7:
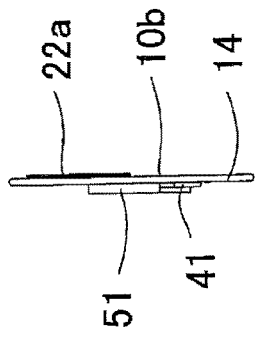
Figure 7:
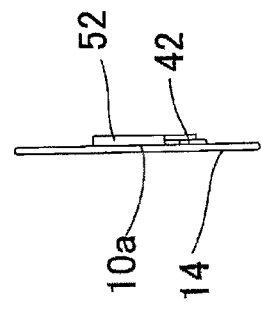
Figure 7:
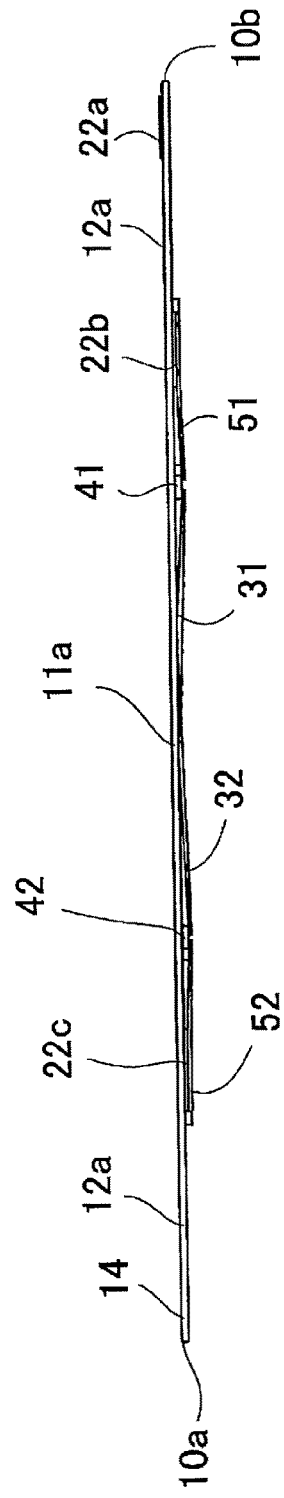
Figure 7:
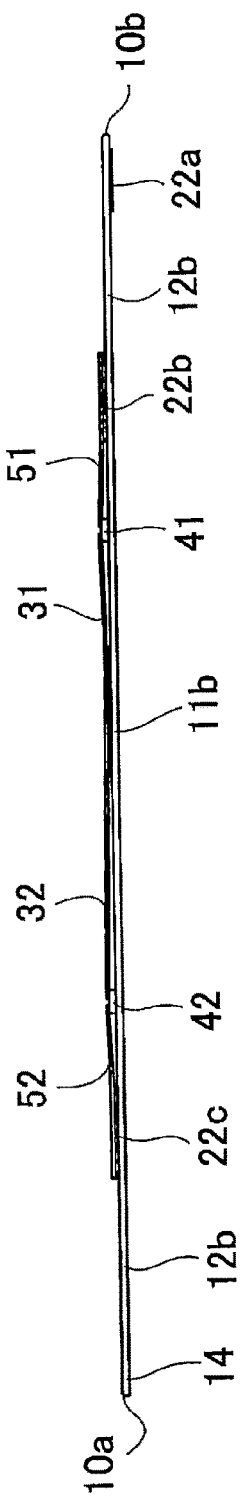

For example, as illustrated in FIG. 7(*a*), the supporter 100 may employ a configuration in which the one end 31*a* of the first auxiliary band section 31 is fixed to one end of the upper side 11*a* (the top end of the left side 11*c*) of the back-contact section 11 on the front surface of the body section 10, the other end 31*b* thereof is fixed to one end of the lateral side (the bottom end of the left side 11*c*) of the back-contact section 11 on the front surface of the body section 10, the one end 32*a* of the second auxiliary band section 32 is fixed to the other end of the upper side 11*a* (the top end of the right side 11*d*) of the back-contact section 11 on the front surface of the body section 10, and the other end 32*b* thereof is fixed to the other end of the lateral side (the bottom end of the right side 11*d*) of the back-contact section 11 on the front surface of the body section 10.

As the cross section of the first auxiliary band section 31 and the second auxiliary band section 32, the configuration in which the second auxiliary band section 32 goes over the first auxiliary band section 31 is illustrated in FIGS. 7(*a*), 7(*e*), and 7(*f*), but a configuration in which the first auxiliary band section 31 goes over the second auxiliary band section 32.

The first auxiliary band section 31 and the second auxiliary band section 32 may have a configuration in which the first auxiliary band section 31 goes over the second auxiliary band section 32 in the cross section in the vicinity of the upper side 11*a* of the back-contact section 11 and the second auxiliary band section 32 goes over the first auxiliary band section 31 in the cross section in the vicinity of the lower side 11*b* of the back-contact section 11, and vice versa.

In this embodiment, the supporter 100 is used as a supporter for the lumbar region, but may be used as a supporter such as an abdominal supporter, a pelvic supporter, or an iliac supporter.

Second Embodiment of the Invention

Figure 8:
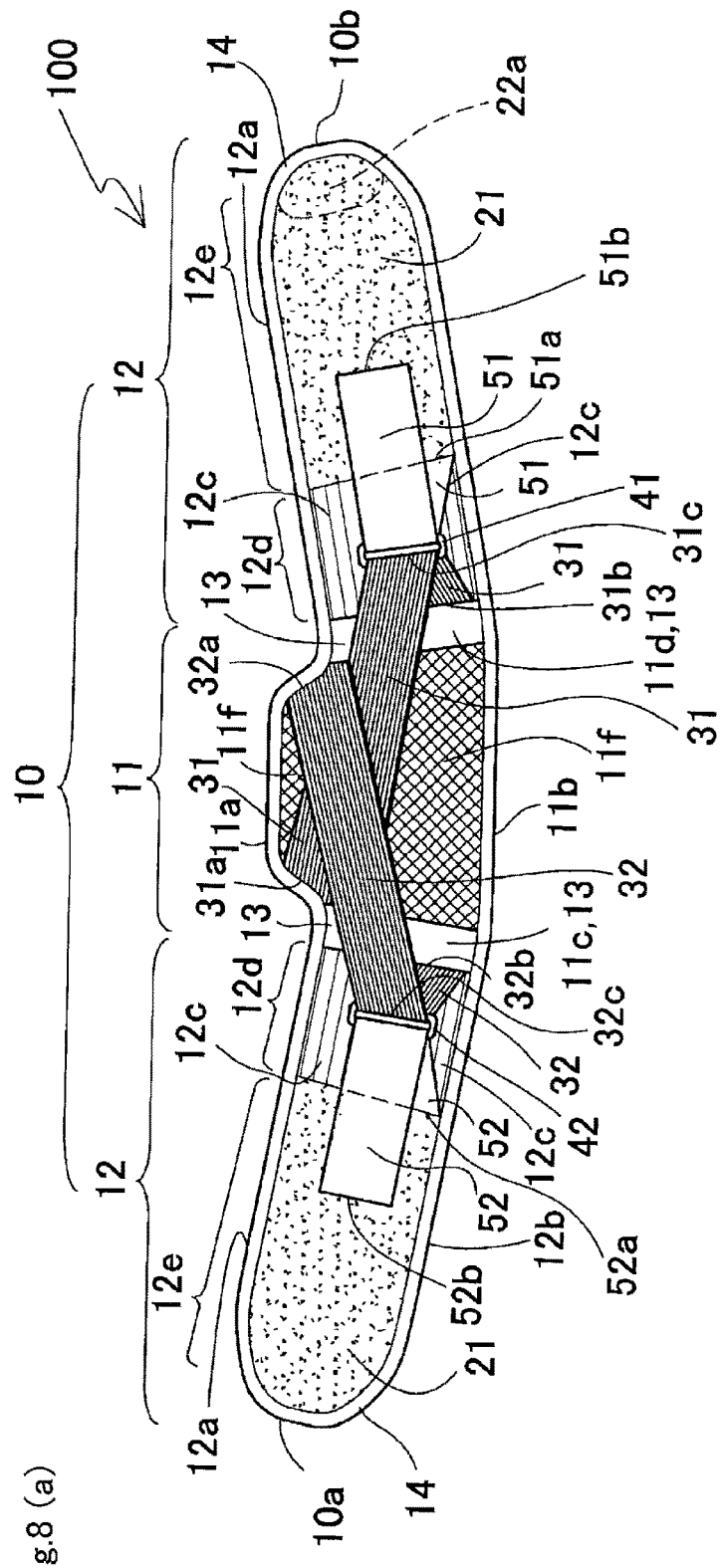
FIG. 8(a) is a diagram illustrating a front surface of a supporter according to a second embodiment.
FIG. 8(b) is a diagram illustrating a lining surface of the supporter illustrated in FIG. 8(a)
FIG. 8(c) is a left side view of the supporter illustrated in FIG. 8(a)
FIG. 8(d) is a right side view of the supporter illustrated in FIG. 8(a)
FIG. 8(e) is an upper side view of the supporter illustrated in FIG. 8(a)
FIG. 8(f) is a lower side view of the supporter illustrated in FIG. 8(a).
Figure 8:
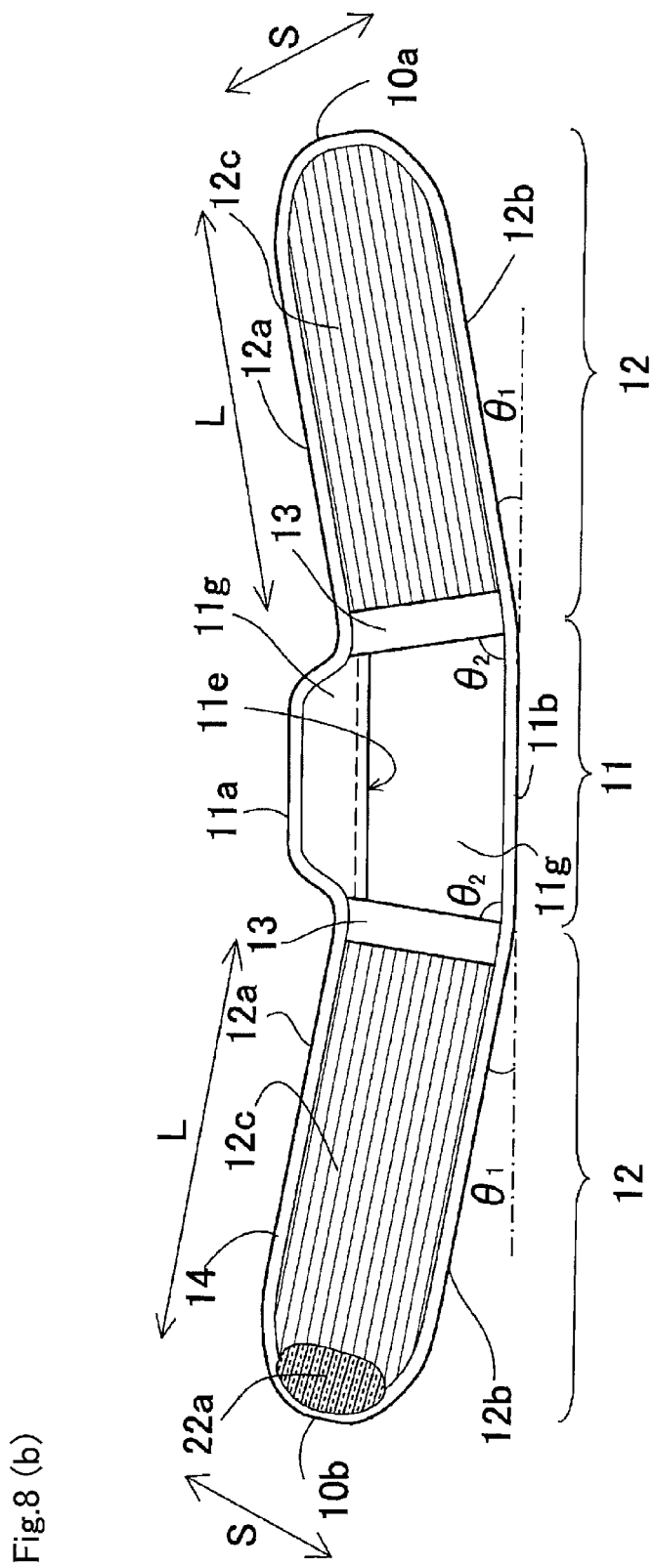
Figure 8:
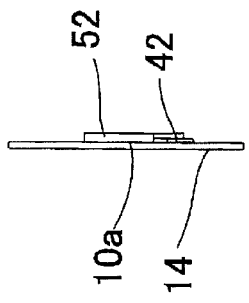
Figure 8:
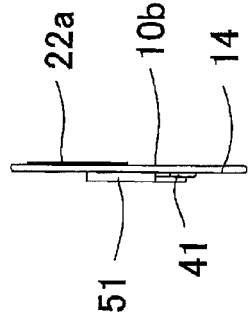
Figure 8:
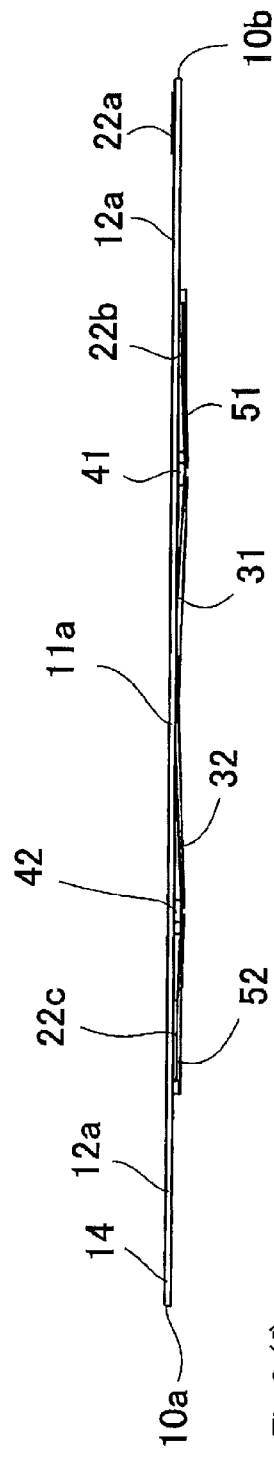
Figure 8:
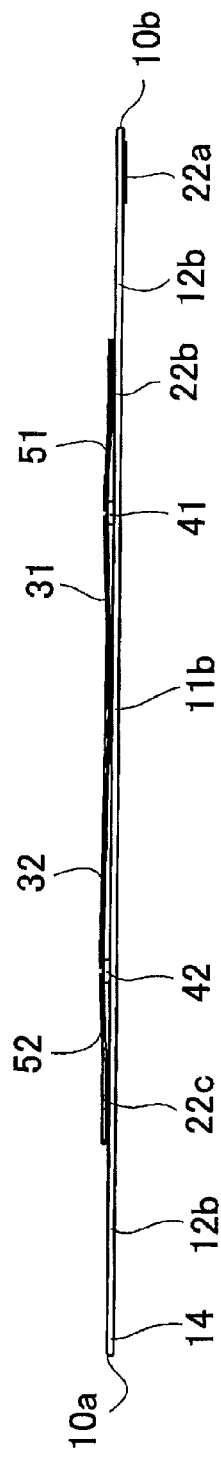
Figure 9:
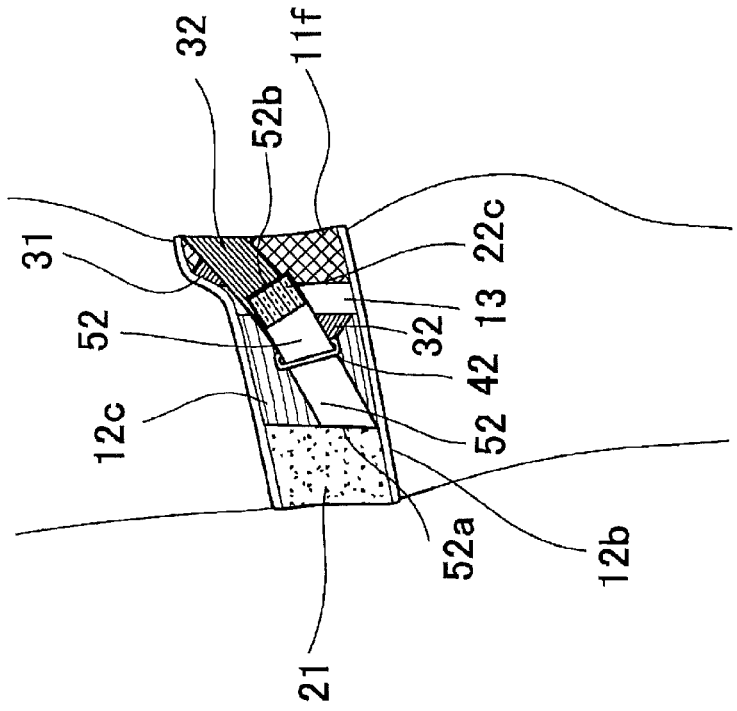
FIG. 9(a) is a front view illustrating a wearing method of the supporter illustrated in FIG. 8.
FIG. 9(b) is a rear view illustrating the wearing method of the supporter illustrated in FIG. 8.
FIG. 9(c) is a left side view illustrating the wearing method of the supporter illustrated in FIG. 8.
FIG. 9(d) is a right side view illustrating the wearing method of the supporter illustrated in FIG. 8.
Figure 9:
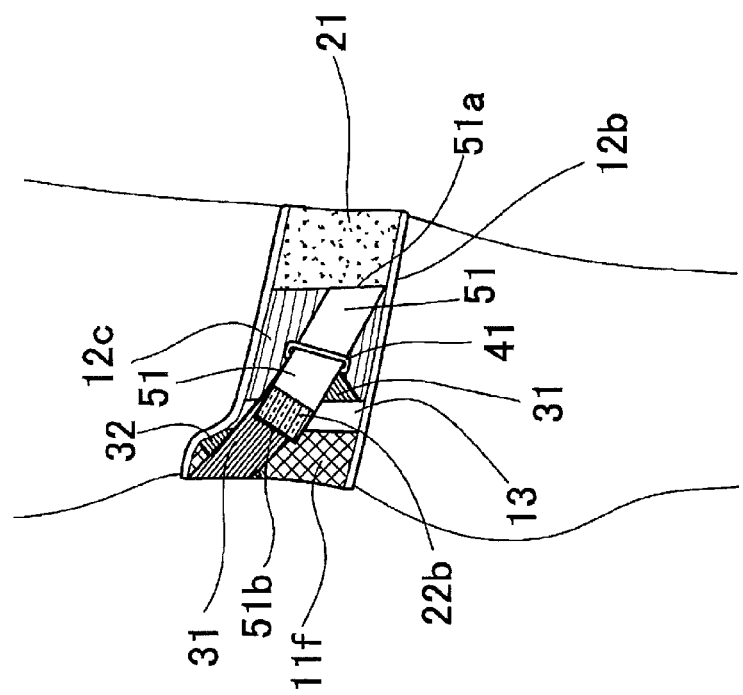

FIG. 8(*a*) is a diagram illustrating a front surface of a supporter according to a second embodiment, FIG. 8(*b*) is a diagram illustrating a lining surface of the supporter illustrated in FIG. 8(*a*), FIG. 8(*c*) is a left side view of the supporter illustrated in FIG. 8(*a*), FIG. 8(*d*) is a right side view of the supporter illustrated in FIG. 8(*a*), FIG. 8(*e*) is an upper side view of the supporter illustrated in FIG. 8(*a*), and FIG. 8(*f*) is a lower side view of the supporter illustrated in FIG. 8(*a*). FIG. 9(*a*) is a front view illustrating a wearing method of the supporter illustrated in FIG. 8, FIG. 9(*b*) is a rear view illustrating the wearing method of the supporter illustrated in FIG. 8, FIG. 9(*c*) is a left side view illustrating the wearing method of the supporter illustrated in FIG. 8, and FIG. 9(*d*) is a right side view illustrating the wearing method of the supporter illustrated in FIG. 8.

Figure 10:
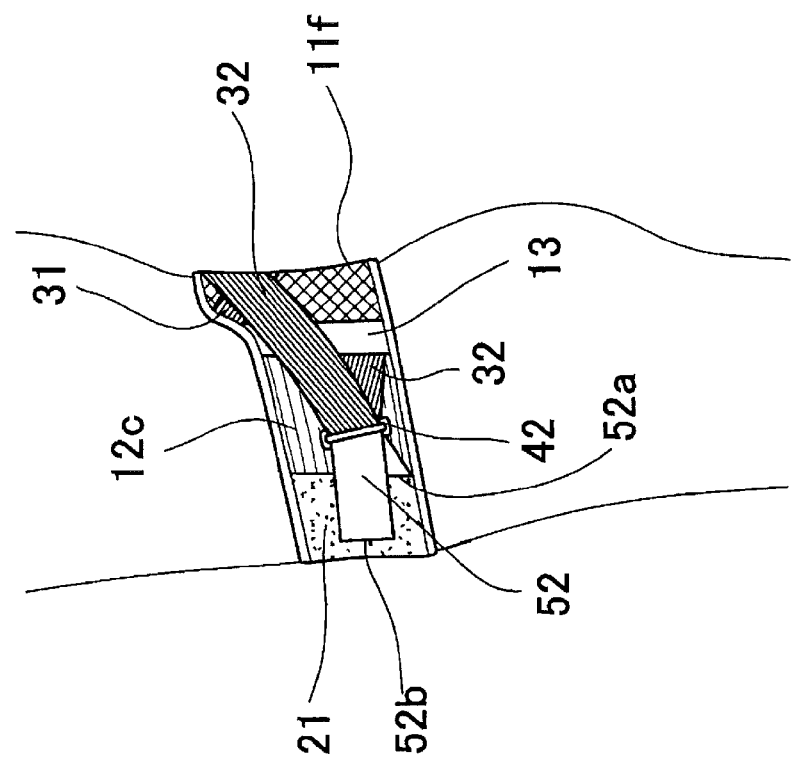
FIG. 10(a) is a front view illustrating a next step of the wearing method of the supporter illustrated in FIG. 9(a)
FIG. 10(b) is a rear view illustrating a next step of the wearing method of the supporter illustrated in FIG. 9(b)
FIG. 10(c) is a left side view illustrating a next step of the wearing method of the supporter illustrated in FIG. 9(c)
FIG. 10(d) is a right side view illustrating a next step of the wearing method of the supporter illustrated in FIG. 9(d).
Figure 10:
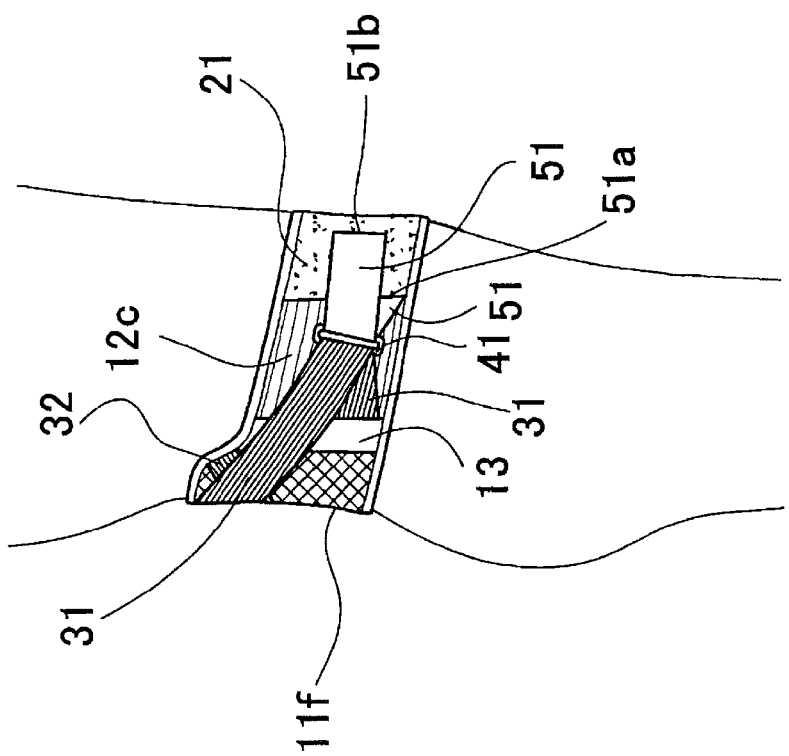

FIG. 10(*a*) is a front view illustrating a next step of the wearing method of the supporter illustrated in FIG. 9(*a*), FIG. 10(*b*) is a rear view illustrating a next step of the wearing method of the supporter illustrated in FIG. 9(*b*), FIG. 10(*c*) is a left side view illustrating a next step of the wearing method of the supporter illustrated in FIG. 9(*c*), and FIG. 10(d) is a right side view illustrating a next step of the wearing method of the supporter illustrated in FIG. 9(d). In FIGS. 8 and 9, the same reference signs as illustrated in FIGS. 1, 5, and 6 denote the same or corresponding elements and description thereof will not be repeated.

One end 51a of the first adjustment band section 51 according to this embodiment is fixed in contact with the lower side 12b side of the non-stretchable portion 12e of the protruding section 12 on the right end 10b side of the body section 10 on the front surface of the body section 10.

One end 52a of the second adjustment band section 52 according to this embodiment is fixed in contact with the lower side 12b side of the non-stretchable portion 12e of the protruding section 12 on the left end 10a side of the body section 10 on the front surface of the body section 10.

The second embodiment is different from the first embodiment, in that the one end 51a of the first adjustment band section 51 and the one end 52a of the second adjustment band section 52 are fixed in contact with the lower side 12b of the non-stretchable portions 12e of the protruding sections 12, and exhibits the same operational advantages as in the first embodiment, except for the operation advantage based on the fixation positions of the one end 51a of the first adjustment band section 51 and the one end 52a of the second adjustment band section 52 described below.

In the first embodiment, in the state illustrated in FIG. 5, the wearer wears the supporter 100 by grasping the other end 51b of the first adjustment band section 51 and the other end 52b of the second adjustment band section 52 with the respective hands and extruding the first adjustment band section 51 and the second adjustment band section 52 forward.

However, some wearers may extrude the first adjustment band section 51 and the second adjustment band section 52 in a direction (hereinafter, referred to as a lower side crossing direction), in which the wearers easily apply a force to the first adjustment band section 51 and the second adjustment band section 52, crossing the lower side 12b of the non-stretchable portion 12e of the protruding section 12 instead of extruding the first adjustment band section 51 and the second adjustment band section 52 forward.

In this case, for example, in the supporter 100 illustrated in FIG. 1, the extending direction of the first adjustment band section 51 between one end 51a of the first adjustment band section 51 and the first ring 41 is different from the direction (the extending direction of the first adjustment band section 51 between the other end 51b of the first adjustment band section 51 and the first ring 41) in which the first adjustment band section 51 is extruded. Similarly, for example, in the supporter 100 illustrated in FIG. 1, the extending direction of the second adjustment band section 52 between one end 52a of the second adjustment band section 52 and the second ring 42 is different from the direction (the extending direction of the second adjustment band section 52 between the other end 52b of the second adjustment band section 52 and the second ring 42) in which the second adjustment band section 52 is extruded.

Accordingly, the first ring 41 and the second ring 42 rotate to follow the operation of extruding the first adjustment band section 51 and the second adjustment band section 52 in the lower side crossing direction, the first auxiliary band section 31, the second auxiliary band section 32, the first adjustment band section 51, and the second adjustment band section 52 are twisted, the pressing force or the tensile load from the first auxiliary band section 31 and the second auxiliary band section 32 to the back-contact section 11 becomes insufficient (uneven), and thus a desired effect of the supporter 100 may not be satisfactorily achieved.

On the contrary, in the supporter 100 according to this embodiment, as illustrated in FIG. 9(c), by fixing the one end 51a of the first adjustment band section 51 in contact with the lower side 12b side of the non-stretchable portion 12e of the protruding section 12, the extending direction of the first adjustment band section 51 between the one end 51a of the first adjustment band section 51 and the first ring 41 is substantially parallel to the direction (the extending direction of the first adjustment band section 51 between the other end 51b of the first adjustment band section 51 and the first ring 41) in which the first adjustment band section 51 is extruded. Similarly, in the supporter 100 according to this embodiment, as illustrated in FIG. 9(d), by fixing the one end 52a of the second adjustment band section 52 in contact with the lower side 12b side of the non-stretchable portion 12e of the protruding section 12, the extending direction of the second adjustment band section 52 between the one end 52a of the second adjustment band section 52 and the second ring 42 is substantially parallel to the direction (the extending direction of the second adjustment band section 52 between the other end 52b of the second adjustment band section 52 and the second ring 42) in which the second adjustment band section 52 is extruded.

Accordingly, without causing the first ring 41 and the second ring 42 to rotate to follow the operation of extruding the first adjustment band section 51 and the second adjustment band section 52 in the lower side crossing direction, the first ring 41 slides over the first adjustment band section 51 and the second ring 42 slides over the second adjustment band section 52. Accordingly, as illustrated in FIG. 10, the first auxiliary band section 31, the second auxiliary band section 32, the first adjustment band section 51, and the second adjustment band section 52 are not twisted and a desired effect of the supporter 100 can be satisfactorily achieved.

Third Embodiment of the Invention

Figure 11:
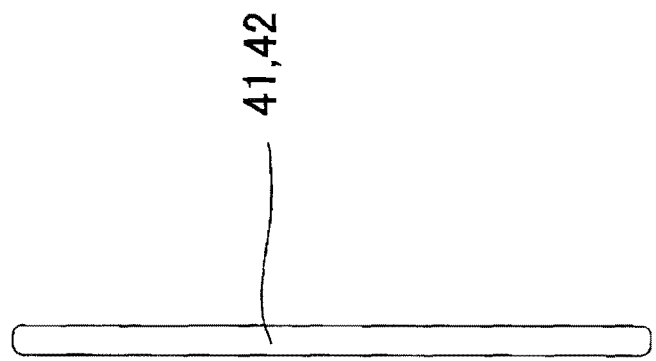
FIG. 11(a) is a front view and a rear view illustrating a first ring and a second ring according to a third embodiment.
FIG. 11(b) is a right side view and a left side view of the first ring and the second ring illustrated in FIG. 11(a)
FIG. 11(c) is a top view and a bottom view of the first ring and the second ring illustrated in FIG. 11(a)
FIG. 11(d) is a partially-enlarged view in the vicinity of the first ring when the first ring and the second ring of the supporter illustrated in FIG. 1(a), FIG. 7(a), and FIG. 8(a) are replaced with the first ring and the second ring illustrated in FIG. 11(a)
FIG. 11(e) is a central cross-sectional view in the partially-enlarged view illustrated in FIG. 11(d).
Figure 11:
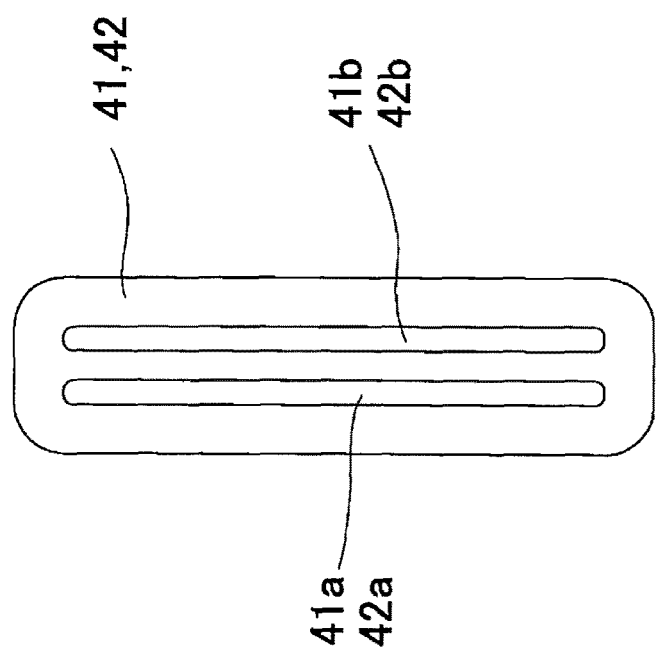
Figure 11:
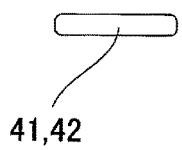
Figure 11:
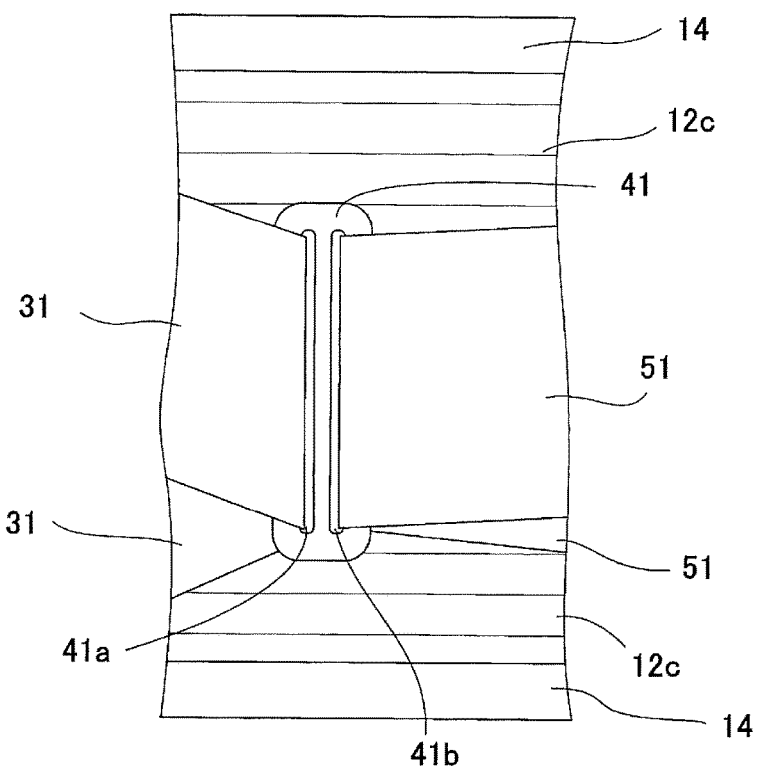
Figure 11:
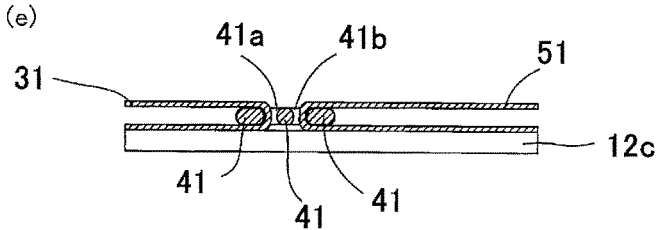

FIG. 11(a) is a front view and a rear view illustrating a first ring and a second ring according to a third embodiment, FIG. 11(b) is a right side view and a left side view of the first ring and the second ring illustrated in FIG. 11(a), FIG. 11(c) is a top view and a bottom view of the first ring and the second ring illustrated in FIG. 11(a), FIG. 11(d) is a partially-enlarged view in the vicinity of the first ring when the first ring and the second ring of the supporter illustrated in FIG. 1(a), FIG. 7(a), and FIG. 8(a) are replaced with the first ring and the second ring illustrated in FIG. 11(a), and FIG. 11(e) is a central cross-sectional view in the partially-enlarged view illustrated in FIG. 11(d). In FIG. 11, the same reference signs as illustrated in FIG. 1 denote the same or corresponding elements and description thereof will not be repeated.

As illustrated in FIGS. 11(a) to 11(c), the first ring 41 according to this embodiment includes two through-holes (a first long hole 41a and a second long hole 41b) formed to correspond to the width and the thickness of the first auxiliary band section 31 and the first adjustment band section 51.

The through-hole corresponding to the width and the thickness of the first auxiliary band section 31 and the first adjustment band section 51 means that the through-hole has such a size that the sliding of the first ring 41 is not affected and the band sections (the first auxiliary band section 31 and the first adjustment band section 51) are not twisted in the through-holes (the first long hole 41a and the second long hole 41b). That is, by setting the length of the through-holes to be substantially equal to the width of the band sections, it is possible to balance a combined force applied from the first auxiliary band section 31 and the first adjustment band section 51 to the first ring 41. In addition, by setting the width of the through-holes to be 1.5 times to 2.0 times the thickness of the band sections, it is possible to prevent the first auxiliary band section 31 and the first adjustment band section 51 from being twisted.

For example, when the width of the first auxiliary band section 31 and the first adjustment band section 51 is set to about 50 mm and the thickness of the first auxiliary band section 31 and the first adjustment band section 51 is set to about 1.5 mm, the length of the first long hole 41a and the second long hole 41b in the first ring 41 is set to about 50 mm and the width of the first long hole 41a and the second long hole 41b in the first ring 41 is set to about 2.5 mm. Then, even when the first adjustment band section 51 is extruded in the lower side crossing direction at the time of wearing the supporter 100, the first adjustment band section 51 can be smoothly extruded in the lower side crossing direction without twisting the first auxiliary band section 31 and the first adjustment band section 51.

In this embodiment, as illustrated in FIGS. 11(d) and 11(e), when the first auxiliary band section 31 is loosely inserted into one through-hole (for example, the first long hole 41a) out of the two through-holes of the first ring 41, the first adjustment band section 51 is loosely inserted into the other through-hole (the second long hole 41b) out of the two through-holes of the first ring 41.

As illustrated in FIGS. 11(a) to 11(c), the second ring 42 according to this embodiment includes two through-holes (a first long hole 42a and a second long hole 42b) formed to correspond to the width and the thickness of the second auxiliary band section 32 and the second adjustment band section 52.

The through-hole corresponding to the width and the thickness of the second auxiliary band section 32 and the second adjustment band section 52 means that the through-hole has such a size that the sliding of the second ring 42 is not affected and the band sections (the second auxiliary band section 32 and the second adjustment band section 52) are not twisted in the through-holes (the first long hole 42a and the second long hole 42b). That is, by setting the length of the through-hole to be substantially equal to the width of the band sections, it is possible to balance a combined force applied from the second auxiliary band section 32 and the second adjustment band section 52 to the second ring 42. In addition, by setting the width of the through-holes to be 1.5 times to 2.0 times the thickness of the band sections, it is possible to prevent the second auxiliary band section 32 and the second adjustment band section 52 from being twisted.

For example, when the width of the second auxiliary band section 32 and the second adjustment band section 52 is set to about 50 mm and the thickness of the second auxiliary band section 32 and the second adjustment band section 52 is set to about 1.5 mm, the length of the first long hole 42a and the second long hole 42b in the second ring 42 is set to about 50 mm and the width of the first long hole 42a and the second long hole 42b in the second ring 42 is set to about 2.5 mm. Then, even when the second adjustment band section 52 is extruded in the lower side crossing direction at the time of wearing the supporter 100, the second adjustment band section 52 can be smoothly extruded in the lower side crossing direction without twisting the second auxiliary band section 32 and the second adjustment band section 52.

In this embodiment, when the second auxiliary band section 32 is loosely inserted into one through-hole (for example, the first long hole 42a) out of the two through-holes of the second ring 42, the second adjustment band section 52 is loosely inserted into the other through-hole (the second long hole 42b) out of the two through-holes of the second ring 42.

As described above in the second embodiment, some wearers may extrude the first adjustment band section 51 and the second adjustment band section 52 in the lower side crossing direction, and a desired effect of the supporter 100 may not be satisfactorily achieved due to the twisting of the first auxiliary band section 31, the second auxiliary band section 32, the first adjustment band section 51, and the second adjustment band section 52.

On the contrary, in the supporter 100 according to this embodiment, the first ring 41 and the second ring 42 each have two through-holes, the first auxiliary band section 31 and the first adjustment band section 51 are loosely inserted into different through-holes (the first long hole 41a and the second long hole 41b) of the first ring 41, respectively, and the second auxiliary band section 32 and the second adjustment band section 52 are loosely inserted into different through-holes (the first long hole 42a and the second long hole 42b) of the second ring 42, respectively.

Accordingly, the auxiliary band sections (the first auxiliary band section 31 and the second auxiliary band section 32) and the adjustment band sections (the first adjustment band section 51 and the second adjustment band section 52) do not interfere with each other, the first ring 41 and the second ring 42 do not rotate, and the band sections (the first auxiliary band section 31, the first adjustment band section 51, the second auxiliary band section 32, and the second adjustment band section 52) are not twisted in the through-holes.

That is, the supporter 100 according to this embodiment, it is possible to prevent the twisting of the first auxiliary band section 31, the second auxiliary band section 32, the first adjustment band section 51, and the second adjustment band section 52 and to satisfactorily achieve the desired effect of the supporter 100.

The third embodiment is different from the first embodiment, in that the first ring 41 and the second ring 42 each have two through-holes, and exhibits the same operational advantages as in the first embodiment, except for the operation advantage based on the two through-holes. By combination with the second embodiment, it is possible to more satisfactorily achieve the desired effect of the supporter 100.

As long as the first ring 41 and the second ring 42 according to this embodiment each have the two through-holes, the entire shape of the rings or the positions or shapes of the first long hole and the second long hole do not need to be symmetric, but it is preferable that the shapes or positions be symmetric as illustrated in FIGS. 11(a) to 11(c), from the viewpoint of production efficiency or low cost. A configuration in which the first ring 41 and the second ring 42 each have three or more through-holes belongs to the scope of the present invention.

Other Embodiments of the Invention

The first auxiliary band section 31 according to this embodiment includes a first sewed portion sewed to the stretchable portion 12d (the power net fabric 12c).

The position of the first sewed portion has only to be in the vicinity of the bent portion 31c from the substantial midpoint between the other end 31b and the bent portion 31c in the state (see FIGS. 1(a), 7(a), and 8(a)) in which the supporter 100 is arranged flat with the first auxiliary band section 31 having a natural length, and the first sewed portion is preferably arranged in the vicinity of about 20 mm from the bent portion 31c so as to cross the first auxiliary band section 31 substantially in parallel to the longitudinal direction of the through-holes of the first ring 41. Examples of the yarn used for the first sewed portion include polyester yarn, polyurethane yarn, polypropylene yarn, and nylon yarn.

The first sewed portion according to this embodiment is arranged to cross the first auxiliary band section 31 substantially in parallel to the longitudinal direction of the through-holes of the first ring 41, but may be arranged in a scattered-dot shape or may be partially arranged so as not to cross the first auxiliary band section 31, as long as the first sewed portion is arranged substantially in parallel to the longitudinal direction of the through-holes of the first ring 41.

The second auxiliary band section 32 according to this embodiment includes a second sewed portion sewed to the stretchable portion 12d (the power net fabric 12c).

The position of the second sewed portion has only to be in the vicinity of the bent portion 32c from the substantial midpoint between the other end 32b and the bent portion 32c in the state (see FIGS. 1(a), 7(a), and 8(a)) in which the supporter 100 is arranged flat with the second auxiliary band section 32 having a natural length, and the second sewed portion is preferably arranged in the vicinity of about 20 mm from the bent portion 32c so as to cross the second auxiliary band section 32 substantially in parallel to the longitudinal direction of the through-holes of the second ring 42. Examples of the yarn used for the second sewed portion include polyester yarn, polyurethane yarn, polypropylene yarn, and nylon yarn.

The second sewed portion according to this embodiment is arranged to cross the second auxiliary band section 32 substantially in parallel to the longitudinal direction of the through-holes of the second ring 42, but may be arranged in a scattered-dot shape or may be partially arranged so as not to cross the second auxiliary band section 32, as long as the second sewed portion is arranged substantially in parallel to the longitudinal direction of the through-holes of the second ring 42.

As described above in the second embodiment, some wearers may extrude the first adjustment band section 51 and the second adjustment band section 52 in the lower side crossing direction, and a desired effect of the supporter 100 may not be satisfactorily achieved due to the twisting of the first auxiliary band section 31, the second auxiliary band section 32, the first adjustment band section 51, and the second adjustment band section 52.

On the contrary, in the supporter 100 according to this embodiment, since the first auxiliary band section 31 and the second auxiliary band section 32 are sewed to the stretchable portions 12d, respectively, the movable regions of the first ring 41 and the second ring 42 are limited. Accordingly, it is possible to suppress rotation of the first ring 41 and the second ring 42 and thus to satisfactorily achieve the desired effect of the supporter 100 without twisting the first auxiliary band section 31, the second auxiliary band section 32, the first adjustment band section 51, and the second adjustment band section 52.

This embodiment is different from the first embodiment, in that the first auxiliary band section 31 and the second auxiliary band section 32 are sewed to the stretchable portions 12d, respectively, and exhibits the same operational advantages as in the first embodiment, except for the operational advantage based on the first sewed portion and the second sewed portion. By combination with the second embodiment and/or the third embodiment, it is possible to more satisfactorily achieve the desired effect of the supporter 100.

REFERENCE SIGNS LIST

10: body section
10a: left end
10b: right end
11: back-contact section
11a: upper side
11b: lower side
11c: left side
11d: right side
11e: opening
11f: raschel mesh
11g: crochet-knitted fabric
12: protruding section
12a: upper side
12b: lower side
12c: power net fabric
12d: stretchable portion
12e: non-stretchable portion
13: grosgrain tape
14: binder tape
20: hook-and-loop fastener
21: loops
22a, 22b, 22c: hooks
31: first auxiliary band section
31a: one end
31b: the other end
31c: bent portion
32: second auxiliary band section
32a: one end
32b: the other end
32c: bent portion
41: first ring
41a: first long hole
41b: second long hole
42: second ring
42a: first long hole
42b: second long hole
51: first adjustment band section
51a: one end
51b: the other end
52: second adjustment band section
52a: one end
52b: the other end
60: pressing section
61: upper bottom
62: lower bottom
63: concave portion
100: supporter
201: lumbar vertebrae
202: pelvis
203: abdominal cavity
204: sacrum
205: ilium
206: sacroiliac joint
207: rib

What is claimed is:

1. A supporter formed of a band-shaped member, the supporter comprising:
a back-contact section that is arranged substantially at the center of the band-shaped member, and that is adapted to come in contact with a wearer's back region;

protruding sections that are arranged at both sides of the back-contact section;

a pair of auxiliary band sections that defines two band-shaped members having stretchability in a longitudinal direction and in which an annular ring is arranged to be slidable over each band-shaped member; and a pair of adjustment band sections that defines two band-shaped members having stretchability lower than the stretchability of the auxiliary band sections, wherein each protruding section includes a stretchable portion being in contact with the back-contact section and having stretchability in the longitudinal direction and a non-stretchable portion having no stretchability, wherein both ends of the pair of auxiliary band sections are fixed so that the two band-shaped members cross each other on the back-contact section, wherein each of the pair of adjustment band sections is slideably inserted into the annular rings arranged in the auxiliary band sections, and wherein the pair of adjustment band sections includes:

a first adjustment band section in which one end of the band-shaped member is fixed to the non-stretchable portion of the right protruding section and an other end of the band-shaped member is able to be fastened to the non-stretchable portion of the right protruding section, and a second adjustment band section in which one end of the band-shaped member is fixed to the non-stretchable portion of the left protruding section and an other end of the band-shaped member is able to be fastened to the non-stretchable portion of the left protruding section.

2. The supporter according to claim 1, wherein a body section includes the back-contact section and the protruding sections and adapted to cause a lining surface thereof to contact the wearer's lumbar region and to surround the lumbar region, wherein the non-stretchable portions of each protruding section are arranged adjacently to the stretchable portion, wherein the pair of auxiliary band sections that defines the two band-shaped members includes:

a first auxiliary band section in which one end of the band-shaped member is fixed to a left end of an upper side of the back-contact section on a front surface of the body section and the other end of the band-shaped member is fixed to one of a bottom end of a right side of the back-contact section on the front surface of the body section or a bottom end of a lateral side in contact with the back-contact section in the stretchable portion of the protruding section on the right end side of the body section on the front surface of the body section, and a second auxiliary band section in which one end of the band-shaped member is fixed to a right end of the upper side of the back-contact section on the front surface of the body section and the other end of the band-shaped member is fixed to one of a bottom end of the left side of the back-contact section on the front surface of the body section or a bottom end of the lateral side in contact with the back-contact section in the stretchable portion of the protruding section on the left end side of the body section on the front surface of the body section, wherein the annular ring includes an annular first ring arranged in the first auxiliary band section and an annular second ring arranged in the second auxiliary band section, wherein the first adjustment band section is formed so that one end of the band-shaped member is fixed to the non-stretchable portion of the protruding section on the right end side of the body section on the front surface of the body section and the other end of the band-shaped member is able to be fastened to the non-stretchable portion of the protruding section on the right end side of the body section on the front surface of the body section after being slideably inserted into the first ring, and wherein the second adjustment band section is formed so that one end of the band-shaped member is fixed to the non-stretchable portion of the protruding section on the left end side of the body section on the front surface of the body section and the other end of the band-shaped member is able to be fastened to the non-stretchable portion of the protruding section on the left end side of the body section on the front surface of the body section after being slideably inserted into the second ring.

3. The supporter according to claim 2, wherein a natural length of the first auxiliary band section is greater than a gap between the left end of the upper side of the back-contact section and the bottom end of the right side of the back-contact section, and wherein a natural length of the second auxiliary band section is greater than a gap between the right end of the upper side of the back-contact section and the bottom end of the left side of the back-contact section.

4. The supporter according to claim 2, wherein the two band-shaped members of the pair of auxiliary band sections that defines the two band-shaped members cross each other in the vicinity of the upper side of the back-contact section.

5. The supporter according to claim 2, further comprising a pressing section formed of a plate-shaped member not having stretchability, wherein the back-contact section is a bag shaped body having an opening and the pressing section is inserted into and extracted from the bag shaped body.

6. The supporter according to claim 2, wherein one end of each of the two band-shaped members of the pair of adjustment band sections that defines the two band-shaped members is fixed in contact with a lower side of the non-stretchable portion of the corresponding protruding section.

7. The supporter according to claim 2, wherein each annular ring includes at least two through-holes formed to correspond to the widths and the thicknesses of the auxiliary band sections and the adjustment band sections, wherein the auxiliary band section is slideably inserted into one through-hole of the at least two through-holes, and wherein the adjustment band section is slideably inserted into the other through-hole of the at least two through-holes.

8. The supporter according to claim 1, wherein a body section includes the back-contact section and the protruding sections and adapted to cause a lining surface thereof to contact the wearer's lumbar region and to surround the lumbar region, wherein the non-stretchable portions of each protruding section are arranged adjacently to the stretchable portion, wherein the pair of auxiliary band sections that defines the two band-shaped members includes:

a first auxiliary band section in which one end of the band-shaped member is fixed to a left end of an upper side of the back-contact section on a front surface of the body section and the other end of the band-shaped member is fixed to one of a bottom end of a left side of the back-contact section on the front surface of the body section or a bottom end of a lateral side in contact with the back-contact section in the stretchable portion of the protruding section on the left end side of the body section on the front surface of the body section, and a second auxiliary band section in which one end of the band-shaped member is fixed to a right end of the upper side of the back-contact section on the front surface of the body section and the other end of the band-shaped member is fixed to one of a bottom end of the right side of the back-contact section on the front surface of the body section or a bottom end of the lateral side in contact with the back-contact section in the stretchable portion of the protruding section on the right end side of the body section on the front surface of the body section, wherein the annular ring includes an annular first ring arranged in the first auxiliary band section and an annular second ring arranged in the second auxiliary band section, wherein the first adjustment band section is formed so that one end of the band-shaped member is fixed to the non-stretchable portion of the protruding section on the right end side of the body section on the front surface of the body section and the other end of the band-shaped member is able to be fastened to the non-stretchable portion of the protruding section on the right end side of the body section on the front surface of the body section after being slideably inserted into the first ring, and wherein the second adjustment band section is formed so that one end of the band-shaped member is fixed to the non-stretchable portion of the protruding section on the left end side of the body section on the front surface of the body section and the other end of the band-shaped member is able to be fastened to the non-stretchable portion of the protruding section on the left end side of the body section on the front surface of the body section after being slideably inserted into the second ring.

9. The supporter according to claim 8, wherein a natural length of the first auxiliary band section is greater than a gap between the left end of the upper side of the back-contact section and the bottom end of the right side of the back-contact section, and wherein a natural length of the second auxiliary band section is greater than a gap between the right end of the upper side of the back-contact section and the bottom end of the left side of the back-contact section.

10. The supporter according to claim 8, wherein the two band-shaped members of the pair of auxiliary band sections that defines the two band-shaped members cross each other in the vicinity of the upper side of the back-contact section.

11. The supporter according to claim 8, further comprising a pressing section formed of a plate-shaped member not having stretchability, wherein the back-contact section is a bag shaped body having an opening and the pressing section is inserted into and extracted from the bag shaped body.

12. The supporter according to claim 8, wherein one end of each of the two band-shaped members of the pair of adjustment band sections that defines the two band-shaped members is fixed in contact with a lower side of the non-stretchable portion of the corresponding protruding section.

13. The supporter according to claim 8, wherein each annular ring includes at least two through-holes formed to correspond to the widths and the thicknesses of the auxiliary band sections and the adjustment band sections, wherein the auxiliary band section is slideably inserted into one through-hole of the at least two through-holes, and wherein the adjustment band section is slideably inserted into the other through-hole of the at least two through-holes.

14. The supporter according to claim 1, wherein the two band-shaped members of the pair of auxiliary band sections that defines the two band-shaped members cross each other in the vicinity of the upper side of the back-contact section.

15. The supporter according to claim 1, further comprising a pressing section formed of a plate-shaped member not having stretchability, wherein the back-contact section is a bag shaped body having an opening and the pressing section is inserted into and extracted from the bag shaped body.

16. The supporter according to claim 1, wherein one end of each of the two band-shaped members of the pair of adjustment band sections that defines the two band-shaped members is fixed in contact with a lower side of the non-stretchable portion of the corresponding protruding section.

17. The supporter according to claim 1, wherein each annular ring includes at least two through-holes formed to correspond to the widths and the thicknesses of the auxiliary band sections and the adjustment band sections, wherein the auxiliary band section is slideably inserted into one through-hole of the at least two through-holes, and wherein the adjustment band section is slideably inserted into the other through-hole of the at least two through-holes.

18. The supporter according to claim 1, wherein the protruding sections include tips which protrude upward, and toward right and left from both sides of the back-contact section, wherein both ends of the pair of auxiliary band sections are fixed to an upper side of the back-contact section and to one of (i) bottom ends of lateral sides of the back-contact section and (ii) bottom ends of the lateral sides in contact with the back-contact section in the stretchable portions of the protruding sections so that the two band-shaped members cross each other on the back-contact section.

19. The supporter according to claim 18, wherein a body section includes the back-contact section and the protruding sections and adapted to cause a lining surface thereof to contact the wearer's lumbar region and to surround the lumbar region, wherein the non-stretchable portions of each protruding section are arranged adjacently to the stretchable portion, wherein the pair of auxiliary band sections that defines the two band-shaped members includes:

a first auxiliary band section in which one end of the band-shaped member is fixed to a left end of the upper side of the back-contact section on a front surface of the body section and the other end of the band-shaped member is fixed to one of a bottom end of a right side of the back-contact section on the front surface of the body section or a bottom end of a lateral side in contact with the back-contact section in the stretchable portion of the protruding section on the right end side of the body section on the front surface of the body section, and a second auxiliary band section in which one end of the band-shaped member is fixed to a right end of the upper side of the back-contact section on the front surface of the body section and the other end of the band-shaped member is fixed to one of a bottom end of the left side of the back-contact section on the front surface of the body section or a bottom end of the lateral side in contact with the back-contact section in the stretchable portion of the protruding section on the left end side of the body section on the front surface of the body section, wherein the annular ring includes an annular first ring arranged in the first auxiliary band section and an annular second ring arranged in the second auxiliary band section, wherein the first adjustment band section is formed so that one end of the band-shaped member is fixed to the non-stretchable portion of the protruding section on the right end side of the body section on the front surface of the body section and the other end of the band-shaped member is able to be fastened to the non-stretchable portion of the protruding section on the right end side of the body section on the front surface of the body section after being slideably inserted into the first ring, and wherein the second adjustment band section is formed so that one end of the band-shaped member is fixed to the non-stretchable portion of the protruding section on the left end side of the body section on the front surface of the body section and the other end of the band-shaped member is able to be fastened to the non-stretchable portion of the protruding section on the left end side of the body section on the front surface of the body section after being slideably inserted into the second ring.

20. The supporter according to claim 18, wherein a body section includes the back-contact section and the protruding sections and adapted to cause a lining surface thereof to contact the wearer's lumbar region and to surround the lumbar region, wherein the non-stretchable portions of each protruding section are arranged adjacently to the stretchable portion, wherein the pair of auxiliary band sections that defines the two band-shaped members includes:

a first auxiliary band section in which one end of the band-shaped member is fixed to a left end of the upper side of the back-contact section on a front surface of the body section and the other end of the band-shaped member is fixed to one of a bottom end of a left side of the back-contact section on the front surface of the body section or a bottom end of a lateral side in contact with the back-contact section in the stretchable portion of the protruding section on the left end side of the body section on the front surface of the body section, and a second auxiliary band section in which one end of the band-shaped member is fixed to a right end of the upper side of the back-contact section on the front surface of the body section and the other end of the band-shaped member is fixed to one of a bottom end of the right side of the back-contact section on the front surface of the body section or a bottom end of the lateral side in contact with the back-contact section in the stretchable portion of the protruding section on the right end side of the body section on the front surface of the body section, wherein the annular ring includes an annular first ring arranged in the first auxiliary band section and an annular second ring arranged in the second auxiliary band section, the first adjustment band section is formed so that one end of the band-shaped member is fixed to the non-stretchable portion of the protruding section on the right end side of the body section on the front surface of the body section and the other end of the band-shaped member is able to be fastened to the non-stretchable portion of the protruding section on the right end side of the body section on the front surface of the body section after being slideably inserted into the first ring, and wherein the second adjustment band section is formed so that one end of the band-shaped member is fixed to the non-stretchable portion of the protruding section on the left end side of the body section on the front surface of the body section and the other end of the band-shaped member is able to be fastened to the non-stretchable portion of the protruding section on the left end side of the body section on the front surface of the body section after being slideably inserted into the second ring.

* * * * *